United States Patent [19]

Whitson-Fischman

[11] Patent Number: 5,162,037
[45] Date of Patent: Nov. 10, 1992

[54] MAGNETICALLY INFLUENCED HOMEOPATHIC PHARMACEUTICAL FORMULATIONS, METHODS OF THEIR PREPARATION AND METHODS OF THEIR ADMINISTRATION

[75] Inventor: Walter Whitson-Fischman, New York, N.Y.

[73] Assignee: Whitson Laboratories, Inc., New York, N.Y.

[21] Appl. No.: 696,759

[22] Filed: May 7, 1991

Related U.S. Application Data

[63] Continuation-in-part of Ser. No. 540,295, Jun. 19, 1990, abandoned, which is a continuation of Ser. No. 176,731, Apr. 1, 1988, abandoned.

[51] Int. Cl.⁵ ............................................. A61N 2/00
[52] U.S. Cl. ...................................... 600/12; 600/15; 128/907
[58] Field of Search ................ 600/9, 12, 15; 128/907

[56] References Cited

U.S. PATENT DOCUMENTS

| 2,671,451 | 3/1954 | Bolger | 128/260 |
| 4,501,726 | 2/1985 | Shröder et al. | 424/1.1 |

FOREIGN PATENT DOCUMENTS

| 0000667 | 2/1979 | European Pat. Off. | |
| 0035932 | 9/1981 | European Pat. Off. | |
| 0208362 | 1/1987 | European Pat. Off. | |
| 1467974 | 1/1969 | Fed. Rep. of Germany | |
| 1492136 | 9/1969 | Fed. Rep. of Germany | |
| 2062080 | 7/1971 | Fed. Rep. of Germany | |
| 3634121 | 11/1987 | Fed. Rep. of Germany | |
| 2258839 | 8/1975 | France | |
| 60032716 | 7/1983 | Japan | |
| 61-115015 | 6/1986 | Japan | |
| 63-159313 | 7/1988 | Japan | |
| 1147411 | 3/1985 | U.S.S.R. | 600/12 |
| 1335297 | 9/1987 | U.S.S.R. | 600/9 |
| 1264511 | 2/1972 | United Kingdom | |
| WO78/00005 | 12/1978 | World Int. Prop. O. | |

OTHER PUBLICATIONS

Orekhov et al., "Prevention . . . Aspirin", The Lancet, Sep. 5, 1987.

*Primary Examiner*—Lee S. Cohen
*Attorney, Agent, or Firm*—Edgar H. Haug; John M. Kilcoyne

[57] ABSTRACT

A method for treating pathogenic conditions of the human body by preparing a homeopathic mixture of at least one herb, herbal extract or other compound exhibiting therapeutic properties, adding a magnetically permeable substance to the mixture if necessary, magnetizing the resulting mixture to impart a substantially unipolar magnetic charge on the mixture and administering the magnetized mixture through one or more specific acupuncture points associated with producing a desired response to the particular condition being treated. The invention is also directed to the treatment of various diseases through the oral, auricular, topical or injectable administration of magnetically influenced homeopathic medicaments.

38 Claims, 3 Drawing Sheets

MAGNETICALLY INFLUENCED HOMEOPATHIC PHARMACEUTICAL FORMULATIONS, METHODS OF THEIR PREPARATION AND METHODS OF THEIR ADMINISTRATION

FIELD OF THE INVENTION

This application is a continuation-in-part of application Ser. No. 540,295, filed Jun. 19, 1990, abandoned, which in turn is a continuation of application Ser. No. 176,731, filed Apr. 1, 1988, abandoned.

This invention relates to homeopathic medicaments and methods for the treatment of illness and injury in human beings using such homeopathic medicaments.

More particularly, the invention relates to homeopathic methods of treatment of conditions including illnesses, pathogenic diseases, allergies, chemical and hormonal imbalances, addictive chemical dependencies, and physical injuries to the human body. The methods of treatment include oral, topical, auricular and injectable forms of homeopathic formulations which are magnetically treated or influenced during administration to a patient through specific acupuncture points.

BACKGROUND OF THE INVENTION

Homeopathy is an ancient healing art and forms a vital part of medical therapy. The practice of homeopathy is widespread, particularly in eastern cultures and many European countries. Homeopathic medicine teaches the use of natural based remedies and, as such, provides an alternative to traditional allopathic medicine which relies heavily on the use of petrochemical based pharmaceuticals. There has been a large increase in interest in homeopathic medicine in the United States in recent years due, in large part, to a growing disenchantment with allopathic medications and the complications and side effects arising from their use. Frequently, the administration of allopathic medications results in serious side effects more deleterious to the patient than the basic condition being treated. Today, more and more individuals are looking for a gentler, safer path to good health free of the risks and side effects associated with traditional allopathic medicines. Furthermore, such medicines are often prohibitively expensive, particularly for patients who are indigent or elderly.

Homeopathic remedies, on the other hand, use pharmaceutical preparations based on the use of herbs or herbal extracts. Homeopathic remedies function in a totally different manner than chemical-based pharmaceuticals in that they do not require administering high concentrations of active ingredients to produce the desired effects. Traditional allopathic pharmaceuticals can be thought of as working quantitatively, that is, the results achieved are generally proportional to the potency and frequency of the dosage administered. By comparison, homeopathic pharmaceuticals can be thought of as working qualitatively in that even the minutest quantities of their active ingredients produce a therapeutic effect by inducing natural body mechanisms to return to their proper level of activity characteristic of a healthful or uninjured state. Homeopathic remedies function by inducing natural body mechanisms and processes to return to their optimum healthful level of operation, that is, their natural biological "set points".

Through our modern understanding of genetics, each bodily member and process is seen as the result of codes programmed into each individual cell. Homeopathic medicine seeks to utilize natural substances, particularly herbs, to induce naturally and gently the body to restore its equilibrium, that is, for all function and processes to return to their set points. Homeopathic medicine looks upon illness and disease as being a state of disequilibrium from the body's optimal set points. A fundamental precept of homeopathic medicine is that a small force or stimulating agent can produce disproportionally greater results, if optimally and effectively applied. Thus, proper administration of a small quantity of a homeopathic medicine can have a large effect in restoring the body to its proper state of equilibrium.

A further advantage of homeopathic medicaments is that they are relatively inexpensive as compared to traditional chemical-based pharmaceuticals. Another fundamental precept in the formulation of homeopathic pharmaceuticals is that repetitive dilution from an original concentrate does not diminish efficacy of the formulation. Thus, large quantities of homeopathic pharmaceuticals can be prepared from a relatively small amount of starting solution. Further, the starting ingredients themselves are natural and relatively inexpensive. The formulation of solutions of homeopathic pharmaceuticals is also a relatively simple process.

Additionally, homeopathy utilizes various medicaments in extremely dilute form. For example, all the medicines used in accordance with the present invention are generally used at a potency of $30\times$ which is a 1–10 dilution taken to the 30th power.

One of the long standing adjustments that was made long ago was a determination of exactly what materials are suitable as diluents. The list is small and primarily restricted to 200 proof Ethyl alcohol, distilled water, sugar and milk sugar. With the possible exception of distilled water, none of these are really totally inert. All the others contribute some identity of their own. As a matter of fact, both sugar and milk sugar are listed as medicants (when in homeopathic dilution) in the homeopathic materia medica.

One example of a homeopathic medicament is extract of pineal gland. As noted in the technical text, "The Pineal Gland" by Russel J. Reiter (Raven Press, N.Y. 1984), the pineal gland occupies a unique physiological niche. Its function has been described as being "the regulator of regulators". The primary action of the pineal gland is believed to be to "govern or restrict the production and/or the secretion of hormones from other endocrine glands."

Since conventional allopathic medications utilize massive chemical intervention as the modus operandi with the actual destruction of the offending pathogen as the ultimate goal, there is little possibility for an interface between the powerful but very subtle activity of the pineal gland and the mighty action of petrochemicals. Homeopathy, however, since it is a vastly more subtle form of medication, appears to be able to intensify the actions of the pineal.

To make the base tincture of the pineal gland, one portion of a freeze dried animal sample of the gland itself is comminuted and then macerated in pure ethanol for ten days with daily agitation. At the end of this time, the extract is filtered. An equal sample of the same material is added to distilled water, brought to a slow simmer and maintained at this point while it is allowed to steep for one hour. At the end of this time, the water extract is also filtered.

Equal amounts of the alcohol and the water extracts are combined to form the base tincture.

In contrast, the manufacture of traditional chemical-based pharmaceuticals generally involves a complicated and costly chemical manufacturing process. Moreover, because the effectiveness of such traditional chemical-based pharmaceuticals resides in the potency of the formulation administered, dilution of the pharmaceutical to a lower potency results in reduced effectiveness. Generally, all such chemical-based pharmaceuticals must be formulated at or near the concentration level or potency at which they will ultimately be administered. Thus, in order to produce large quantities of a pharmaceutical, proportionately large manufacturing facilities are required, which only further adds to the expensiveness of the chemical-based pharmaceuticals utilized in classical allopathic medicine.

Another ancient and long accepted healing art is acupuncture which is believed to have originated in the Orient. Acupuncture involves the relief of symptoms and the cure of illness and injury by the controlled stimulation of points on the human body which regulate or interact with the functioning of specific organs or bodily members to which the acupuncture points are related.

Over the many years that acupuncture has been practiced, specific points on the human body have been determined which regulate or interact with the functioning of all bodily members and processes. Thus, the appropriate points for stimulation for any given condition are known to skilled practitioners in the art.

One particular acupuncture treatment system developed in Japan by Dr. Yoshio Manaka is based on a conception of the human body as encompassing two basic systems, an energetic system and an informational system. The energetic system utilizes the greater portion of energy in the body. The informational system controls the energetic system and response to both external and internal stimuli. Acupuncture is viewed as a therapeutic modality which interacts with and regulates the body's informational system. By influencing the informational system, large changes can be induced with minimal stimulation while allowing the body to function as naturally as possible while its processes are gradually restored to their equilibrium set points.

A recent development in methods of medical treatment has been the discovery of the therapeutic properties of magnetic and electro-magnetic fields and their use in the treatment of illness and injury. Modern science has demonstrated that all living beings exhibit an electro-magnetic field about them. Homeopathic medicine teaches that illness and injury create disturbances to the body's natural electro-magnetic fields. The administration of therapeutic fields restores the body's natural fields to their equilibrium levels. The therapeutic effects of the application of pulsed magnetic fields in the treatment of traumatic injuries to limbs, muscles, tendons, bones and the like, as well as in the treatment of illness such as arthritis, is well-known in the art of medical science.

The human body's susceptibility to magnetic fields is due in large part to the electrolytic properties of many of the chemical constituents of the body. All electrolytic substances are capable of conducting an electric current, and whenever an electric current is flowing a magnetic field is created. The greater the electrolytic properties of the substance, the greater is its conductivity and therefore the greater the resulting magnetic field created during current flow.

The body generates a magnetic field of its own due partly to the presence of iron-carrying charged particles flowing in the blood stream. Other electrolytic substances in the body such as potassium and sodium, in ionic form, are present in substantial amounts and contribute to the body's overall bioelectric/biomagnetic field. It is well known that blood cells are readily polarized when placed in a magnetic field due to the high iron concentration in the blood. Under certain conditions, magnetic fields alter the orientation of blood cells and induce changes in the biological reactions in which they participate, thereby modifying the probability of chemical bond formation.

Human blood is very slightly alkaline with respect to body cells which are more acidic. Magnetic fields can be used to induce reactions which restore the pH of the blood.

For example, in a condition prompted by over-acidity of the blood, that is, one characterized by a low pH, application of magnetic field energy emanating from the north pole of a magnet, which, by convention, is considered to be negative, and which, homeopathically, is considered to be alkaline, helps to restore the blood to its normal pH level.

It has also been shown that the blood's leucocyte count is influenced by magnetic fields. The number of leucocytes in the blood increases depending on prevailing magnetic field conditions.

Therapeutic treatments utilizing magnetic energy operate to produce two curative effects. Therapeutic magnetic fields produce a treatment component which in the case of traumatic physical injury causes a reduction in swelling, a reduction of edema, a draining of fluid build-up due to inflammation and a desensitization to pain.

Therapeutic magnetic energy fields also produce a stimulating component which in the case of traumatic physical injury dilates blood vessels and increases blood circulation, disperses fluid build-up due to inflammation, and strengthens and promotes the healing of damaged tissue.

The application of pulsed magnetic energy has been observed to cause transcutaneous electrical neural stimulation and contributes to the reduction of chronic pain by causing the release of natural pain relieving substance at the spinal cord level and by causing the release of endorphins and ACTH at the pituitary gland level.

As a result of research into the fields of homeopathic pharmaceutical medicine, acupuncture and biomagnetic therapy, a new modality of medical treatment has been developed which combines the features of all three of the above treatment methods in a novel way. Accordingly, a new and unique method of medical treatment has been discovered which is more efficacious than any of the three methods individually as described above.

OBJECTS OF THE INVENTION

Accordingly, a primary object of the present invention is to disclose a new modality of medical therapy which utilizes aspects of homeopathic pharmaceutical therapy, acupuncture therapy and biomagnetic therapy, in combination.

A further object of the invention is to devise a full range of modes of administration of magnetically influenced homeopathic remedies, including topical, injectable, auricular and oral forms.

A further object of the invention is to provide particular homeopathic pharmaceutical formulations for the treatment of specific illnesses, physical injuries and other chemical and hormonal disequilibrium conditions of the human body with precisely determined acupuncture sites to which the homeopathic pharmaceutical remedies are to be applied in the treatment of each specific condition.

A further object of the invention is to provide appropriate means for inducing the biomagnetic field in the homeopathic pharmaceutical remedy for each form of administration.

SUMMARY OF THE INVENTION

The present invention is directed to a method of treatment of human illness and injury by administering to the patient homeopathic medicaments through selected acupuncture points stimulated by a controlled magnetic field. A very broad spectrum of human illness can be effectively treated by homeopathic medicament of the instant invention through selection of the appropriate homeopathic remedy, preparation of a mixture of the homeopathic remedy and a magnetically permeable component and magnetization of the resulting mixture during administration to the patient through specific acupuncture sites.

Various embodiments of the invention include administering therapeutic amounts of the magnetic mixture in oral, injectable, topical and auricular forms. Further, depending upon the condition being treated, the dosage and frequency of administration will vary. In a particularly preferred embodiment, the patient is administered with a regimen of oral, transdermal and injectable dosages.

BRIEF DESCRIPTION OF THE DRAWINGS

Aspects of the present invention are illustrated by the accompanying drawings in which.

DETAILED DESCRIPTION OF PREFERRED EMBODIMENTS OF THE INVENTION

The homeopathic medicaments of the present invention, when administered through specific acupuncture sites, have demonstrated remarkable efficacy in the treatment of a wide range of afflictions, many of which have no known cure in the realm of allopathic medicine. Effective delivery systems for these homeopathic formulations have been devised including topical, injectable, auricular and oral forms.

In accordance with the teaching of the present invention, the homeopathic medicament, when administered as an injectable, is first carefully mixed with an effective amount of a magnetically permeable ingredient. Although numerous compounds are suitable, it has been found that ferrous gluconate is particularly effective. The herb-based homeopathic medicament is then prepared for administration to the patient depending upon the specific delivery system used. During administration to the patient, the medicament, whether or not it is mixed with a magnetically permeable ingredient, is charged or influenced by a magnetic field which imparts a unipolar charge to the medicament as it enters the body through a pre-selected acupuncture point. Since a magnet has two poles, to effect a unipolar charge to the medicament, the poles of the delivery devices are separated. The medicament and the body are only exposed to one pole. The other pole is outside of, or away from, the body. In this way, the medicament is exposed to the influence of only one pole. Such application of a magnetic charge at, or in close proximity to, the acupuncture site is believed to stimulate or activate the acupuncture site thereby enhancing the therapeutic efficacy of the medicaments being administered.

Acupuncture points can be stimulated with heat, electricity, ultrasound, laser beams, mechanical vibration, etc. However, stimulation by magnetism has been found to be one of the most effective, and yet, at the same time, is one of the most benign.

Particularly effective results have been achieved when applying relatively small levels of magnetic charge in the range of 1 to 10 gauss to the medicament as it is being administered into the acupuncture point. Such low levels of magnetic flux can aptly be described as homeopathic. It has further been found that the most effective acupuncture sites are located in the arms and legs below the elbow and knee, respectively. These points are commonly referred to as "command points" and are well known to those skilled in the art.

Having described the invention in its most fundamental terms, the various forms of administration of medicaments will now be described in detail. Reference is made to the accompanying figures where appropriate.

Figure 3:
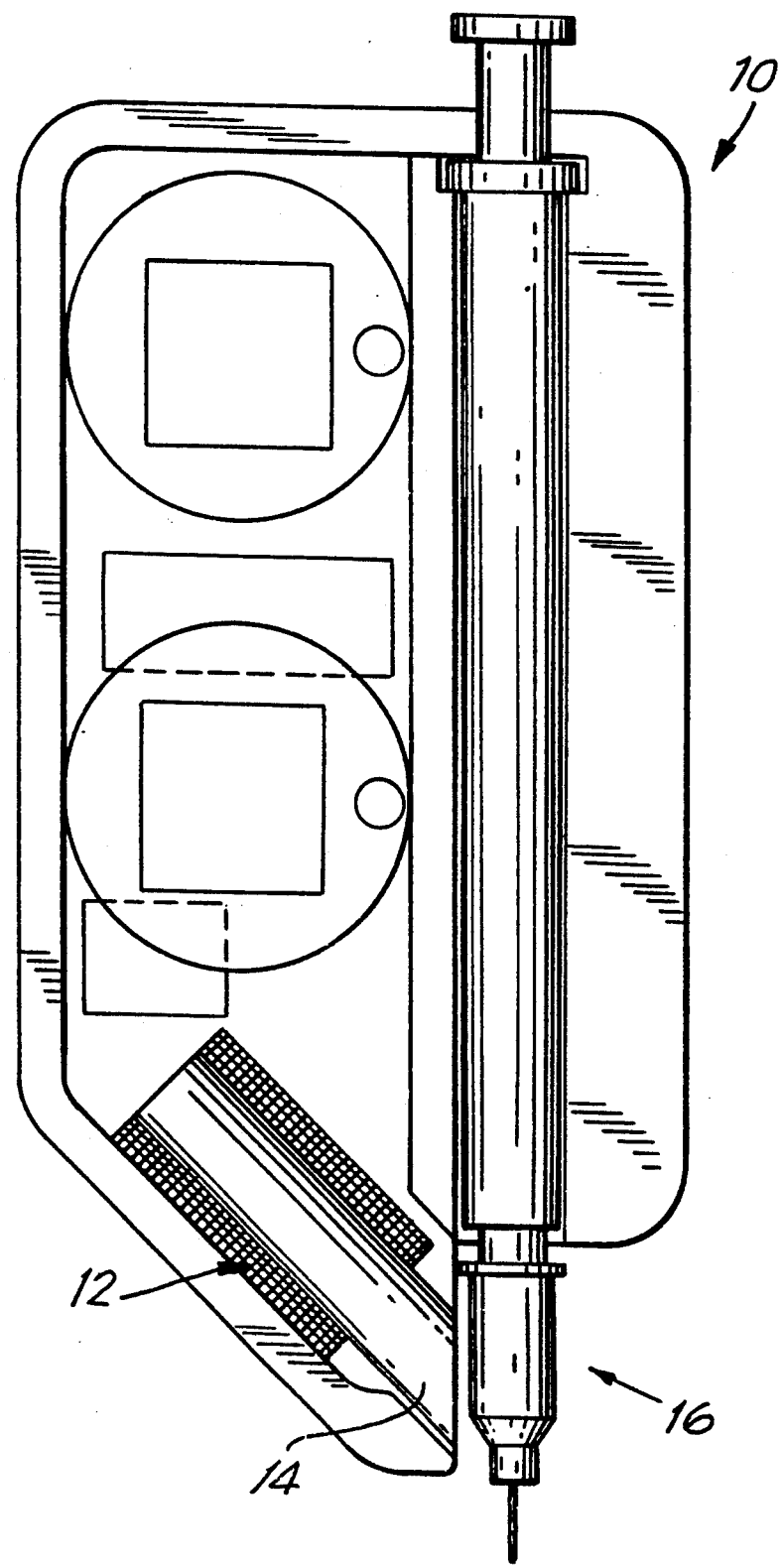
FIG. 3 shows a preferred embodiment for imparting a magnetic field to the injectable form of the homeopathic medicaments.

One delivery system used is by injection. The formulation dosage and duration of treatment for the injectable medicaments is described in detail in the formulation examples which follow. Since it has been observed that injecting homeopathic medicaments demonstrate unexpected and significantly enhanced efficacy when a unipolar magnetic charge is imparted to the medicament during administration or injection into an acupuncture point, a device has been developed to enable the administering physician to suitably charge the medicament. One such device is shown in FIG. 3.

This device consists of a housing 10. Within the housing 10 is an electronic circuit which delivers a pulsed DC current to the electromagnetic coil 12 with a frequency in the range of about 5 to 10 Hz. The electromagnetic coil 12 is positioned to impart a controlled magnetic charge to core 14. A syringe or hypodermic needle 16 used to inject the homeopathic medicament can be positioned in housing 10 such that the point of the needle or syringe is in close proximity to the end of the core 14 as shown in FIG. 3. The entire length of the hypodermic needle is magnetized. The end of the needle which is to enter the skin at the acupuncture point is given the desired charge. Each molecule of the medicament going down the needle receives a magnetic charge. Although the charge dissipates when it hits the skin, during the instant before this happens, the acupuncture point is stimulated by being bombarded by a series of magnetic impulses.

Figure 2:
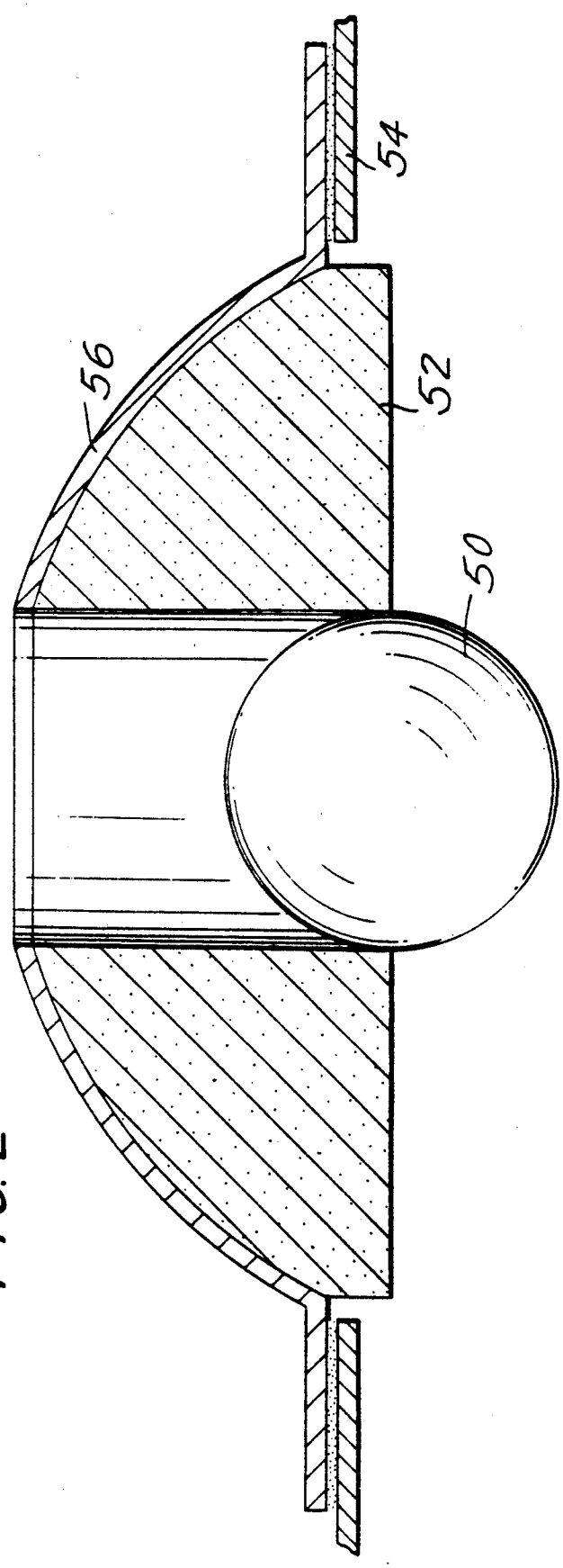
FIG. 2 shows an embodiment for the topical administration of a homeopathic medicament.

Another alternative delivery system used is the topical. One particularly preferred topical system is illustrated in FIG. 2. The topical patch 52 is made of a porous material such as sintered metal capable of absorbing a therapeutic amount of homeopathic medicament. The patch 52 has an extended opening therethrough on the underside of which is tightly fitted a metal sphere or ball 50 which can readily accept and retain a magnetic charge. Suitable materials used to prepare the metal sphere or ball 50 include iron, steel and other ferrous alloys that are magnetically efficient. The patch 52 can then be impregnated with a therapeutic amount of desired homeopathic medicament. A unipolar magnetic charge is then imparted to the metallic core 50 of patch 52 after it is affixed to a suitable acupuncture point.

In one embodiment, the patch is a dome shaped "donut" shaped device with a hole in the center as shown in FIG. 2. The patch is formed by a metal sintering process and is made of a stainless steel alloy that is virtually non-magnetic. Because it is made of sintered metal, the device is porous and can be impregnated with a liquid solution of the desired medication as described later. On the underside of the device, the ball bearing 50 is press fitted into place within the opening so that it partially projects below the surface. The ball is made of a ferrous alloy that is extremely permeable magnetically and will also retain the magnetic charge. The ball typically is not formed by the sintering process, and it is not porous so it will not absorb any liquid medication. The patch can be mounted on a circle of surgical adhesive tape 56, all of which can be protected by one or more "peel off" strips of release paper 54 similar to the type used with adhesive bandages.

Still another form of administering homeopathic medicaments is orally.

Figure 1:
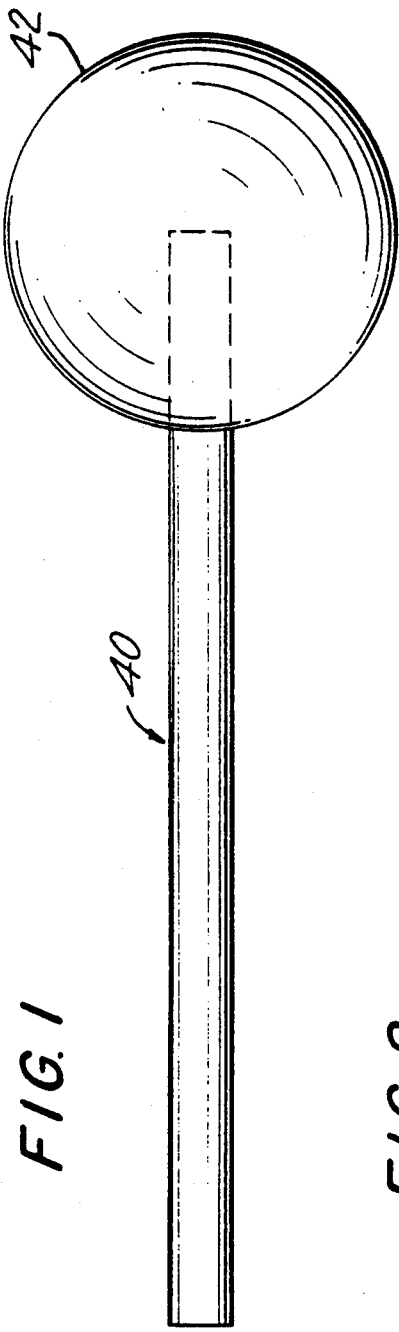
FIG. 1 shows a preferred embodiment of an oral delivery vehicle for the administration of homeopathic medicaments.

With reference to FIG. 1, this oral device can aptly be described as a medicinal "lollipop" consisting of a rod portion 40 and a ball or bulbous portion 42. In one embodiment, the rod 40 is made up of a stainless steel alloy that is capable of holding a magnetic charge. The ball portion 42 can have an inert core. The ball portion 42 can also be coated with a homeopathic composition made of ferrous gluconate mixed with sugar to a dilution in the range of 3× to 4×. It can then be impregnated with an alcohol tincture containing the desired homeopathic medicament of the desired homeopathic dilution. The entire device can be encased in a sanitary wrapping. To use the "lollipop", the entire device in its wrapping if desired, is first placed in a suitable electromagnetic field. In this way, all of the metallic elements of the device are magnetized with one end of the rod portion being charged with one polarity and the other end of the rod portion being charged with the opposite polarity. In this manner, the therapeutic portion of the device having a desired unipolar charge can influence the ball portion which is placed under the tongue of the patient in order to contact the acupuncture points in the mouth.

In a specific embodiment, the "handle" or rod 40 of the "lollipop" is made of a stainless steel or ferrous metal of such alloy that will readily accept magnetism and will hold the charge well. At one end, the metal rod 40 is forced into a hole in the ball portion 42 formed of sintered stainless steel. The specific stainless steel alloy used to form the ball is magnetically transparent so that it will not readily accept a magnetic charge. The alloy is also porous so that it can be impregnated with an alcoholic tincture of the desired homeopathic therapeutic remedy in the desired potency.

The "lollipop" oral delivery device can be positioned under the tongue in the same way an oral thermometer is used. It will directly influence three specific acupuncture points. They are: Jin Jin (which translates as Golden Fluid), Yu-Yeh (Jade Fluid) and Hai Chuen (Sea Spring). The first two are located on the left and right sides of the vinculum lingua when the tongue is rolled up. The third point is under the tongue on the midline about 1/16th inch up from the vinculum lingua.

As a result of this procedure, the acupuncture points in the patient's mouth, and especially those located under the tongue, are influenced by a homeopathic medication whose action has been intensified through the use of the polarized magnetic force.

It is not necessary that the oral device actually contact the acupuncture points as long as it is placed under the tongue in the general area. The sub lingual acupuncture points under the tongue will be influenced by the homeopathic medication with which the ball has been impregnated.

Simultaneously the same sites will also be influenced by the selected unipolar magnetic force. The portion of the "stick" that has been charged with the undesired polarity is outside of the mouth during this entire procedure to prevent any influence of the opposite and undesired magnetic charge. At the conclusion of the period of treatment, the entire device is discarded.

Figure 4:
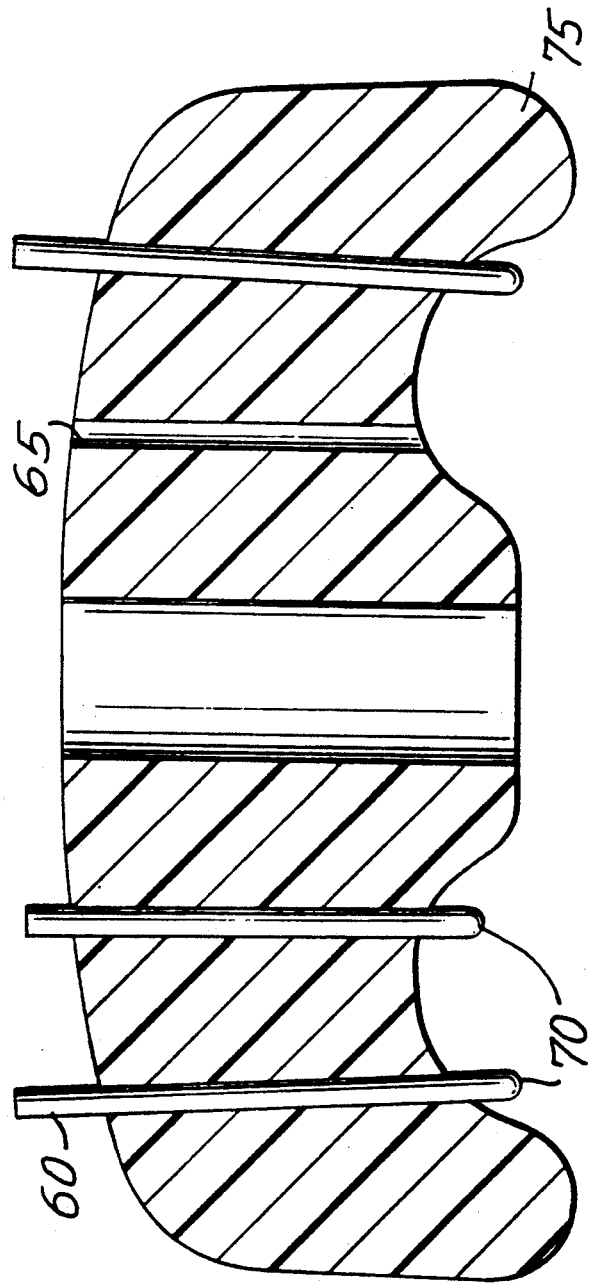
FIG. 4 shows a cross-sectional view through a mold of an ear, with pins inserted therein, for the auricular administration of a homeopathic medicament.

Yet another form of administering the homeopathic medicaments is by auricular measures. An auricular device is illustrated in FIG. 4. In one such device, a mold 75 is made of a patient's ear by gently pressing standard mold compound into place so that it takes on the anatomical contours of the ear and is about ⅛ to ¼ inches thick. The mold material is carefully removed so as to preserve the features of the material and is cured; to the consistency of firm rubber.

Small rods 60 formed of sintered stainless steel, in a ferrous alloy that is magnetically efficient, are fitted through holes punched in the ear mold. The holes 65 coincide with the specific acupuncture points in the ear that are to be influenced. The rods have a rounded point 70 on one end and are sufficiently long as to extend through the mold and firmly contact the auricular acupuncture points.

Prior to use, the sintered metal rods are impregnated with the desired homeopathic medicament as described elsewhere and then dried. They are positioned in the holes pierced in the molds using forceps to avoid contamination. The molds are placed back on the patient's ears and then the desired magnetic charge is induced.

Impregnating with Medicament

In certain preferred embodiments, the sintered metal donut of the patch, and the ball of the oral lollipop, are porous so that they will absorb an alcohol tincture of the medicament after which they are dried and packaged.

Merely soaking the metal may not be effective. Instead, in one embodiment, the sintered metal pieces can be placed into a suitable container with enough alcohol tincture added to completely cover them. The entire system goes into a vacuum chamber and a vacuum then pulled producing an intense surge of tiny bubbles rising to the surface as an indication that, in the lowered atmospheric pressure, the air entrapped in the interstices of the sintered metal is being forced out.

After about ten minutes of vacuum, the container and contents are allowed to return to normal atmosphere. When this happens, the alcohol tincture is forced into the minute pores of the sintered metal parts. After about ten minutes the metal pieces absorb all the tincture that they will accept. Since the air was forced out of the pores of the metal when the container was under vacuum, it can only be replaced by the tincture when normal pressure returns because the sintered metal pieces remain completely submerged in the solution.

In a particularly preferred embodiment, all the medicaments used are at a 30× potency. The dilution sequence used to achieve the 30× potency in this embodiment is carried out with 99+% ethanol.

With respect to the transdermal patch, after being impregnated with the desired medication and then dried, each transdermal patch can be mounted on a circle of surgical adhesive tape that has a hole punched in the center. The hole in the top surface of the patch is aligned with the hole in the adhesive tape. The remainder of the adhesive tape surface can be covered and protected by one or more "peel-off" strips of release paper of a similar type to that used in the well known adhesive bandages. The paper strips are formed with cut-out segments so that the metal donut will project through.

For convenience, the transdermal patches are packaged in a paper envelope and supplied in pairs since the units are often applied bilaterally to acupuncture points on the patient's limbs.

To use the transdermal device, a two-unit package containing patches that have been impregnated with the appropriate medication is chosen. The protective backing from each adhesive circle is removed and the unit is positioned so that the ball bearing on the underside is precisely aligned with the selected acupuncture point on the patient's skin. The unit is affixed to the skin by pressing the rim of adhesive tape (the part that extends beyond the circumference of the donut) firmly against the patient's skin.

When a magnetic charge is applied, the magnetic force will only influence the ball bearing since the donut segment of the unit is formed of an alloy that is not permeable to magnetism. Further, the magnetic charge is applied in such a manner that the portion of the ball in proximity with one end of the electromagnetic coil of an electromagnetic stimulating device is given a charge of one polarity while the bottom portion of the ball that is in contact with the patient's skin automatically assumes the opposite (and therapeutically desirable) charge.

In application, the part of the ball bearing that is in contact with the skin will exert a magnetic force upon the acupuncture point of only the single desired polarity. The opposite magnetic polarity, the one that, for the specific medical purpose, is not as desirable in this instance, is on the opposite (or upper) side of the ball and so does not directly influence the acupuncture point.

The patient leaves the patches in place on his skin for the period of time recommended by his physician (usually 4 to 6 hours) before peeling them off and discarding them.

The following are examples which illustrate embodiments of various aspects of the invention. The examples are provided to illustrate the scope of the invention and are not intended to be limiting. Other applications or aspects of the invention within its broad scope will be apparent to those skilled in the art.

FORMULATION EXAMPLES

A. Injectable

Example 1

An injectable dosage form of an herb-based homeopathic medicament designated FNG-11, for the treatment of fungus and yeast infections, having a homeopathic potency of 30× was prepared from an original concentrated tincture menstruum containing extracts of the herbs *Malaleuca alternifolio, Centella asiatica minor* and *Tacoma conspicua*, extract of citrus seed and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed depending upon the number of acupuncture points being used. The formulations injected were controllably magnetized during administration through the acupuncture sites as described above.

Example 2

An injectable dosage form of an herb-based homeopathic medicament, designated HG-9, for the treatment of intestinal parasites, particularly *Giardia lamblia* and *Entamoeba histolytica*, was prepared from an original concentrated tincture menstruum containing extracts of the herbs *Osbeckia chinensis, Pulsatilla chinensis, Punica granatum, Acalpha australis, Cephaelis ipecacuanha, Picrasma ailanthoides, Asarum sieboldi, Brucea javanica, Magnolia officinalis, Artemisia apiacea, Dichroa febrifuga,* and *Centella asiatica minor*, extract of citrus seed and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 3

An injectable dosage form of an herb-based homeopathic medicament designated VR-27, for the treatment of broad spectrum viral infections, having a homeopathic potency of 30× was prepared from an original concentrated tincture menstruum containing extracts of the herbs *Centella asiatica minor, Pyrrosia lingua, Hypericum perfoliatum, Trichosanthes kirilowii* and *Artemisia apiacea*, and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 4

An injectable dosage form of an herb-based homeopathic medicament designated SPN-7, for the treatment of traumatic injury to muscles, tendons, ligaments, and for the treatment of sprains, was prepared from an original concentrated tincture menstruum containing extracts of the herbs *Panex notoginseng* and *Gynura segetum*, and *Moschus moschiferous* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 5

An injectable dosage form of a homeopathic medicament, designated TYR-10, for the treatment of hypothyroidism, was prepared from an original concentrated tincture menstruum containing an extract of thyroid gland, in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 6

An injectable dosage form of an herb-based homeopathic medicament, designated HRM-4, for the treatment of premenstrual syndrome, menopause, menstrual discomfort and irregularities, and reproductive hormonal imbalance, was prepared from an original concentrated tincture menstruum containing an extract of the herb *Angelica sinensis* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 7

An injectable dosage form of a homeopathic medicament, designated HYT-12, for the treatment of hypothyroidism, was prepared from an original concentrated tincture menstruum containing a solution of iodine crystals and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 8

An injectable dosage form of an herb-based homeopathic medicament for the treatment of nervous tension, designated RLX-22, was prepared from an original tincture menstruum containing extracts of the herbs *Helianthemum canadense*, *Ornithogalum umbellatum*, *Clematis crispa*, *Impatiens pallida*, *Prunus Cerasus* and *Valeriana officinalis*, and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 9

An injectable dosage from of an herb-based homeopathic medicament, designated IMM-2, for restoring and strengthening the body's natural immune system, having a homeopathic potency of 30× was prepared from an original concentrated tincture menstruum containing extracts of the herbs *Panex ginseng, Astragalus membranaceus* and *Rubia cordifolia,* and Snake venom, extract of thymus gland, and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 10

An injectable dosage form of a homeopathic medicament for the treatment of hypoglycemia, designated HYG-6, was prepared from an original concentrated tincture menstruum containing sulfur and vegetable glycerin in 99+% alcohol. The original concentrated tincture was diluted to 29× potency ($10^{-29}$ times the original concentration) with sterile distilled water. Sufficient ferrous gluccanate solution, a magnetically permeable substance, was added to sterile isotonic saline to make a homeopathic potency of $4\times(10^{-4})$. The 29× dilution of the medicament was added to the ferrous gluconate isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 11

An injectable dosage form of an herb-based homeopathic medicament, designated INF-16, for the treatment of bacterial infections, particularly staph and strep, was prepared from an original concentrated tincture menstruum containing extracts of her herbs *Seniccio scandens, Scutellaria baicalensis, Magnolia officinalis, Lonicera japonica, Andrographis paniculata, Centella asiatica minor, Leptotaenia multifida* and *Pupalia geniculata,* and *Moschus moschiferous,* Cow bezoar, Snake's gall and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 12

An injectable dosage from of an herb-based homeopathic medicament, designated FLU-17, for the treatment of viral infections due to colds and influenza, particularly rhino-virus, was prepared from an original concentrated tincture menstruum containing extracts of the herbs *Lonicera confusa, Chrysanthemum indicum, Vitex negundo, Evodia lepta, Ilex asprella, Baphicacanthus cusia* and *Centella asiatica minor,* and *Menthol crystal* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 13

An injectable dosage form of an herb-based homeopathic medicament, designated ALL-5, for the treatment of hayfever and airborne allergies, was prepared from an original concentrated tincture menstruum containing extracts of the herbs *Gentiana lutea, Citrus aurantium, Tanacetum vulgare, Cnicus benedictus, Menyanthes trifoliata, Grindelia robusta, Ephedra sinica, Centipeda minima* and *Centella asiatica minor,* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized at the time of administration through the acupuncture sites as described above.

Example 14

An injectable dosage form of an herb-based homeopathic medicament, designated APN-25, for the treatment of chronic muscular and joint pain, having a homeopathic potency of 5× was prepared from an original concentrated tincture menstruum containing extracts of the herbs *Arnica Montana, Symphytum officianalis, Pupalia geniculata, Rhus Toxicum, Plantago*

*asiatica, Causticum* (a homeopathic medicament prepared from burnt lime), *Helianthemum canadense, Ornithogalum umbellatum, Clematis crispa, Impatiens pallida* and *Prunus Cerasus,* and *Moschus moschiferous,* Cow bezoar, Snake's gall, Germanium dioxide, and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 15

An injectable dosage form of a homeopathic medicament, designated ADR-3, for the treatment of hypoadrenalism, was prepared from an original concentrated tincture menstruum containing extract of adrenal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized at the time of administration through the acupuncture sites as described above.

Example 16

An injectable dosage form of a homeopathic medicament, designated CIR-18, to promote circulation, was prepared from an original concentrated tincture menstruum containing Germanium dioxide and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized at the site of administration through the acupuncture sites as described above.

Example 17

An injectable dosage form of an herb-based homeopathic medicament, designated DTX-28, for the removal of toxicity, was prepared from an original concentrated tincture menstruum containing extracts of the herbs *Nux vomica, Plantago asiatica,* and *Carduus marianus,* and *Germanium dioxide* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 18

An injectable dosage form of an herb-based homeopathic medicament, designated TON-29, for tonification, was prepared from an original concentrated tincture menstruum containing extracts of the herbs *Verbena hastata, Ephedra sinensis, Turner aphrodisiaca, Sabel serrulata, Hydrocotyle asiatica, Linosma ovata, Panex ginseng* and *Echinacea angustifolia,* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 19

An injectable dosage form of an herb-based homeopathic medicament, designated OPT-37, for the treatment of senile macular degeneration, was prepared from an original concentrated texture menstruum containing extracts of the herbs *Euphrasia officinalis, Pupalia geniculata, Ginkgo biloba, Vaccinium myrtillus* and *Hypericum perforiatum,* and *Moschus moschiferous,* Cow bezoar, Snake's gall and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4 \times (10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 20

An injectable dosage form of an herb-based homeopathic medicament, designated LVB-38, for the treatment of liver disfunction, was prepared from an original concentrated tincture menstruum containing extracts of the herbs *Desmodium stracifolium* and *Carduus marianus*, and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 21

An injectable dosage form of an herb-based homeopathic medicament, designated TMR-41, for the reduction of tumors, was prepared from the original concentrated tincture menstruum containing extracts of the herbs *Hypericum japonicum, Prunella vulgaris, Chrysanthemum indicum, Linum usitatissimum, Ulmus fulva, Nymphaea odorata* and *Centella asiatica* minor, and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 22

An injectable dosage form of an herb-based homeopathic medicament, designated ISC-43, for the treatment of inflammatory conditions and rouleau cell formation, was prepared from the original concentrated tincture menstruum containing extracts of the herbs *Ilex pubescents, Salvia multiorrhiza, Andrographis paniculata, Ganoderma japonicum, Pupalia geniculata* and *Centella asiatica* minor, and *Moschus moschiferous*, Cow bezoar, Snake's gall, *Germanium dioxide* and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

Example 23

An injectable dosage form of an herb-based homeopathic medicament, designated TBR-44, for the treatment of tuberculosis, was prepared from an original concentrated tincture menstruum containing extracts of the herbs *Centella asiatica* minor and *Artemesia apiacea*, and Tuberculinum (homeopathic tincture) and extract of pineal gland in 99+% alcohol. The original concentrated tincture was diluted to 29× potency ($10^{-29}$ times the original concentration) with sterile distilled water. Sufficient ferrous gluconate solution, a magnetically permeable substance, was added to sterile isotonic saline to make a homeopathic potency of $4\times(10^{-4})$. The 29× dilution of the medicament was added to the ferrous gluconate/isotonic saline solution to prepare the final 30× medicament. The purpose of the ferrous gluconate/isotonic saline solution is to enable the final medicament to hold a magnetic charge when it is passed through a magnetic field. Injectable dosage portions of 0.2 cc volumes were set aside as needed. The formulations injected were controllably magnetized during administration through the acupuncture sites as described above.

B. Oral Form

Example 24

An oral dosage form of the herb-based homeopathic medicament FNG-11, having the components as in Example 1 above, having a homeopathic potency of 30×, was prepared in accordance with the procedure described above in connection with impregnating the lollipop illustrated in FIG. 1. Similarly, a transdermal dosage form was prepared also as described above.

Example 25

An oral or transdermal dosage form of the herb-based homeopathic medicament HG-9, having the components as in Example 2, having a homeopathic potency of 30×, was prepared according to the method of Example 24.

Example 26

An oral or transdermal dosage form of the herb-based homeopathic medicament VR-27, having the components as in Example 3, having a homeopathic potency of 30×, was prepared according to the method of Example 24.

Example 27

An oral or transdermal dosage form of the herb-based homeopathic medicament SPN-7, having the components as in Example 4, having a homeopathic potency of 30×, was prepared according to the method of Example 24.

Example 28

An oral or transdermal dosage form of the homeopathic medicament TYR-10, having the components as in Example 5, having a homeopathic potency of 30×, was prepared according to the method of Example 24.

Example 29

An oral or transdermal dosage form of the herb-based homeopathic medicament HRM-4, having the components as in Example 6, having a homeopathic potency of 30×, was prepared according to the method of Example 24.

Example 30

An oral or transdermal dosage form of the homeopathic medicament HYT-12, having the components as in Example 7, having a homeopathic potency of 30×, was prepared according to the method of Example 24.

Example 31

An oral or transdermal dosage form of the herb-based homeopathic medicament RLX-22, having the components as in Example 8, having a homeopathic potency of 30×, was prepared according to the method of Example 24.

Example 32

An oral or transdermal dosage form of the herb-based homeopathic medicament IMM-2, having the components as in Example 9, having a homeopathic potency of 30×, was prepared according to the method of Example 24.

Example 33

An oral or transdermal dosage form of the homeopathic medicament HYG-6, having the components as in Example 10, having a homeopathic potency of 30×, was prepared according to the method of Example 24.

Example 34

An oral or transdermal dosage form of the herb-based homeopathic medicament INF-16, having the components as in Example 11, having a homeopathic potency of 30×, was prepared according to the method of Example 24.

Example 35

An oral or transdermal dosage form of the herb-based homeopathic medicament FLU-17, having the components as in Example 12, having a homeopathic potency of 30×, was prepared according to the method of Example 24.

Example 36

An oral or transdermal dosage form of the herb-based homeopathic medicament ALL-5, having the components as in Example 13, having a homeopathic potency of 30×, was prepared according to the method of Example 24.

Example 37

An oral or transdermal dosage form of the herb-based homeopathic medicament APN-25, having the components as in Example 14, having a homeopathic potency of 30×, was prepared according to the method of Example 24.

Similarly, oral or transdermal dosage forms of the homeopathic medicaments as in Examples 15–23, having homeopathic potency of 30×, were prepared according to the method of Example 24.

CLINICAL EXAMPLES

AIDS Study Protocol

This study program ran for about 60 weeks comprising the therapeutic phase. Many patients continued on and participated in the maintenance/prophylaxis aspect for a total participation of approximately 2½ years.

Example 38

The treatment regimen in this example utilized a series of specifically prepared homeopathic medicaments formulated from totally natural botanicals, minerals and other natural substances, and compounded into highly dilute (30×) homeopathic preparations. Each material was used in triad form: an injectable, an oral and a transdermal patch.

The list of these special medicaments together with the condition treated is as follows:

| | |
|---|---|
| IMM-2 | immunity boost |
| ADR-3 | adrenal insufficiency |
| HG-9 | intestinal parasites |
| TYR-10 | thyroid regulation |
| FNG-11 | *Candida albicans*/other systemic fungus infections |
| INF-16 | bacterial infection |
| FLU-17 | common cold, flu |
| CIR-18 | circulatory problems |
| RLX-22 | tension and nervousness |
| APN-25 | pain in muscles, tendons, ligaments |
| VR-27 | viral infections |
| DTX-28 | detoxification |
| TON-29 | general tonic |
| OPT-37 | optical problems (Guillain-Barre Syndrome) |
| LVB-38 | liver boost |
| TMR-41 | internal tumors |
| ISC-43 | red cell "clumping" |
| TBR-44 | tuberculosis |

COMPONENTS OF TREATMENT

Injection

Homeopathic medicaments were injected into the body at specific acupuncture points. A 0.2 cc quantity was introduced into each bilateral point with a 30 ga ½" needle. For example, the bi-lateral acupuncture point used in conjunction with VR-27, the anti-viral, is identified on traditional Chinese charts as TW-5. Other points used with different Homeopathic medicaments for treating peripheral conditions (as noted below) were ST-36,37; SP-6,9; LI-11; GB-34, etc. These points are all categorized in Traditional Chinese Medicine as Command Points and are regarded as being especially effective. Further, they were selected on the basis of previous trial and error applications to determine which would be most effective for each specific malady. Generally, only one pair of points was used to treat each disease entity. All of the injection sites are located distally to the knee and elbow. As a result, they were easily located through the use of anatomical landmarks and present little risk of injury to the patient.

Oral Medication

In addition to being given a series of injections, each patient received oral (lollipop) homeopathic medication. The therapeutic component consisted of the same botanical herbs that comprised the injectable medication. This medication format was also in the highly dilute form traditionally characteristic of all homeopathic medicaments.

Topical Application

The third treatment modality was a transdermal patch that was taped to the skin directly over the appropriate acupuncture points. The patches contained the same formulations in the same highly dilute form as noted above, compounded into a preparation suitable for this type of application.

Thus, the complete therapeutic modality utilized the interlocking action of homeopathy, acupuncture, magnetism and herbalism all of which share a long history of providing effective healing for a wide variety of disease entities. In application, the homeopathic remedies used within this study were introduced into the body by injection via the acupuncture points while their action was reinforced by the parallel use of the same homeopathic medication in oral form and as a transdermal application.

Stimulation

In each of the three forms, the medications delivered to the body were magnetically stimulated at the time of introduction. Like the medicaments themselves, the stimulation was at a homeopathic level.

Treatment of Peripheral Disease Problems

Although this study focused upon the viral component of use of VR-27 as a therapeutic agent, AIDS cannot be considered to be a single disease entity. Usually patients present with a variety of subsidiary symptoms closely associated with the primary viral infection. Commonly seen are such other viral diseases as herpes, CEBV, CMV and hepatitis. Bacterial infections include staphylococcus, streptococcus and chlamydia. Fungal infections include *Candida albicans* in various manifestations. Parasitical infections include *Entamoeba histolytica* and *Giardia lamblia*. *Pneumocyctis carinii* and Syphilis may also be present.

Therefore, although outside the scope of the primary investigation, this test program also employed a parallel series of homeopathic/acupuncture treatments for these associated medical conditions where they existed. The following homeopathic formulations were used for treating the above noted medical conditions:

| | |
|---|---|
| FNG-11 | (for treatment of fungal infections) |
| INF-16 | (for treatment of bacterial infections) |
| HG-9 | (for treatment of intestinal parasites) |
| DTX-26 | (for detoxifying) |
| IMM-2 | (for encouraging the rebuilding of the immune system) |

In addition, other medicaments selected from the other homeopathic medicaments described were used where such applications were indicated.

CRITERIA FOR PATIENT INCLUSION AND EXCLUSION

Inclusion

As primary criteria, the first screening was in accordance with the criteria developed by the Walter Reed Army Hospital to ascertain the presence of AIDS.

As a prime criteria, the patients had to be HIV positive with a Western Blot confirmation.

Further screening was on the basis of:
A. Abnormal number of T-4 lymphocytes and abnormal ratio of T-4 to T-8 lymphocytes under 0.6.
B. Age 18 to 60
C. Ability to provide informed consent
D. Ability to keep all appointments The final group selected included a total of 28 patients. There was a second evaluation procedure for the participants to identify the presence of other medical conditions.

Exclusion

The following categories of patients were excluded from the study:
1. Patients on a treatment regimen that utilized highly potent, toxic or immuno-suppressive drugs such as AZT.
2. Patients receiving medications or supplements of such potency or in sufficient dosage as to interfere with the activity of the homeopathic medications.
3. Patients who were already being treated for life threatening diseases of such severity that, in the opinion of the Administering Physician, they were terminal.

TREATMENT SCHEDULE FOR PATIENTS IN THE STUDY

For the first 52 weeks, the patients were treated twice a week. During this period, two medicaments were generally administered at each visit, with DTX-28 forming a constant along with the regularly scheduled medications. During this period, treatment was semi-customed to address each patient's most pressing medical needs with medicines selected from the following materials:

Anti-Pathogens
VR-27
INF-16
HG-9
FNG-11

According to the patient's pattern of response, the treatment was gradually broadened to include:
Adjunct Medication
IMM-2
ADR-3
TYR-10

After the first 60 weeks, the treatment schedule was modified to once a week. As patients began to show favorable response, Anti-Pathogens were only used on alternate visits with maintenance and prophylaxis medications filling in the blanks in the schedule.

During this phase, when the need for direct therapeutic action was not as intense, some additional medications to deal with specific problems were also used. For example, when there was concern about a possible epidemic of Influenza, all patients were given two treatments with FLU-17. One patient was given OPT-37 to deal with his Guillain-Barre Syndrome.

Maintenance Medication
CIR-18
TON-29
RLX-22
ISC-43

TESTS USED WITHIN THE STUDY FOR PATIENTS ACCEPTED AFTER SCREENING

Each patient received a series of weekly, biweekly and monthly lab tests to provide the tightest possible monitoring of incremental results.

Intake and End-Of-Study Tests

Clinical work-up: Karnofsky score
Laboratory Procedures:
P-24 antigen
Total T-cells+T4/T8 ratio, absolute B-cells
Beta-2-Microblobulin
Neopterin
Circulating Immune Complex, C1Q & C3B
Antibody titers: (IGG & IGM)
    Herpes I & II
    CMV
    EB-VCA
    EBV-EA
    Hepatitis B diagnostic panel
    HIV (quantitative antibody)
    CEIA (Candida antibody)
LA-Candida (Candida antigen)
Complete blood count, differential, platelets, hemoglobin and hematocrit
Sedimentation rate
Urethral smear (male) and vaginal smear (female) for Chlamydia
Rectal swab for parasites
Cryptosporidium (stool sample if diarrhea is present)
Candida quantitative culture (mouth lavage)
Gonorrhea culture (urethral or vaginal)
Syphilis serology—RPR, FTA confirmation quantitative
Chem 25 with liver battery
B12-folic acid-iron assays (if hemoglobin below 10 GM/DL) with reticulocyte count
Urinalysis
Multi-skin tests for DTHS-CMI Multi-Test

Weekly Testing

HIV Antigen (when initially positive)
Antibody titers—(IGG)
    Herpes I & II
    CMV
    EB-VCA
    EBV EA
    Hepatitis B (to follow chronic carriers)
    HIV (quantitative antibody)
    CEIA (Candida antibody)
    FTA (quantitative)
Chem 25 (with liver battery)
Complete blood count, differential, platelets, hemoglobin, and hematocrit (if hemoglobin drops below 10 GM/DL, do anemia profile)
Sedimentation rate
Urinalysis

Interval Testing

Candida quantitative culture (mouth lavage)
Total T-cells+T4/T8 ratio, absolute B-cells
Beta 2-Microblobulin
Multi-skin tests for DTHS-CMI Multi-Test
Neopterin
Rectal swab (for intestinal parasites)

TESTING AND RESULTS

I. Analysis of DTHS—Delayed Type Hypersensitivity Skin Tests

As noted in the Merck Manual (fifteenth edition), the T-cell-mediated portion of the immune system, which is responsible for delayed skin tests and delayed hypersensitivity, is an important defense against malignant cells, viral infections, fungal infections and some bacteria.

Delayed Hypersensitivity Skin Tests are valuable screening tests for T-cell deficiency. The presence of one or more positive delayed skin tests generally indicates an intact T-cell system.

Many HIV studies regard this measurement as one of the most commonly monitored parameters of immune functioning.

The favorable direction of the following statistics is in direct contrast with the usual expectations.

Abstract

Twenty-seven HIV-positive patients enrolled in the study were assessed on the number and total size of positive reactions to skin test antigens for cellular hypersensitivity at five points in time. Results indicated improvement over time with respect to both the number and total size of positive skin test reactions.

Results and Discussion

Tables 1 and 2 give the mean number of reactions, and the mean size of the reactions at each time. Trace reactions refer to values of 0.50 mm. The complete data are provided in Table 3.

TABLE 1

| MEAN NUMBER OF POSITIVE SKIN REACTIONS | | | | | | |
|---|---|---|---|---|---|---|
| | ALL PATIENTS | | PATIENTS IN TREATMENT THROUGH FEBRUARY 1991 | | PATIENTS WITHDRAWING BEFORE FEBRUARY 1991 | |
| | MEAN | N | MEAN | N | MEAN | N |
| INTAKE | 0.26 | 27 | 0.36 | 11 | 0.19 | 16 |
| JAN/FEB 1989 | 0.86 | 22 | 0.57 | 7 | 1.00 | 15 |
| AUGUST 1989 | 2.29 | 14 | 2.30 | 10 | 2.25 | 4 |
| FEBRUARY 1990 | 4.00 | 12 | 3.88 | 8 | 4.25 | 4 |
| FEBRUARY 1991 | 4.55 | 11 | 4.55 | 11 | — | — |

TABLE 2
MEAN TOTAL SIZE OF ALL POSITIVE REACTIONS

| | ALL PATIENTS | | PATIENTS IN TREATMENT THROUGH FEBRUARY 1991 | | PATIENTS WITHDRAWING BEFORE FEBRUARY 1991 | |
|---|---|---|---|---|---|---|
| | MEAN | N | MEAN | N | MEAN | N |
| INTAKE | 0.63 | 27 | 1.00 | 11 | 0.38 | 16 |
| JAN/FEB 1989 | 0.95 | 22 | 0.29 | 7 | 1.27 | 15 |
| AUGUST 1989 | 5.49 | 14 | 6.17 | 10 | 3.80 | 4 |
| FEBRUARY 1990 | 13.13 | 12 | 12.88 | 8 | 13.63 | 4 |
| FEBRUARY 1991 | 10.70 | 11 | 10.70 | 11 | — | — |

NOTE: The two patients with intake at February 1989 are included only in the intake entries (not in the January/February 1990 entries).

TABLE 3
DELAYED HYPERSENSITIVITY SKIN TEST (CMI MULTI SKIN TEST) DATA

| PATIENT # | INTAKE NOV/DEC-88 OR AS NOTED | JAN/FEB-89 10 WEEKS AFTER INTAKE TEST | AUG-89 | FEB-90 | FEB 91 |
|---|---|---|---|---|---|
| 1 | 0/0 | 2/2T | drop-out | 2/6 + 1T | |
| 2 | 0/0 | 3/2.5 + 2T | 3/2.7 + 2T | 5/20.5 | |
| 3 | 0/0 | 0/0 | drop-out | 3/12.5 | |
| 4 | 2/2T (6.89) | | 1/1T | 4/14.5 | 5/12.5 |
| 5 | 0/0 | 2/2T | drop-out | | |
| 6 | 0/0 | 0/0 | 2/1.5 + 1T | 4/15.5 | 4/8 |
| 7 | 1/5 (2/89) | | 2/9.5 | | 4/16 |
| 9 | 1/1T (2/89) | | 1/1T | 4/10.5 | |
| 10 | 0/0 | 0/0 | drop-out | | |
| 11 | 0/0 | 1/1T | drop-out | | |
| 12 | 0/0 | 2/2T | 2/8 | 4/13.5 | 4/12 + 1T |
| 13 | 1/5 (6/89) | | 3/12 | 4/15 | 6/19.75 |
| 14 | 0/0 (6/89) | | 4/12 | 5/14.5 | 4/2 + 3T |
| 15 | 0/0 | 0/0 | 1/1 | absent | 2/7 + 1T |
| 16 | 0/0 | 0/0 | drop-out | | |
| 17 | 0/0 | 0/0 | drop-out | | |
| 18 | 0/0 | 0/0 | died-(Ap-89) | | |
| 19 | 0/0 | 2/2T | drop-out | 2/10 | |
| 20 | 0/0 | -0/0 | 4/9.9 | | 4/10 + 1T |
| 21 | 0/0 | 1/1T | 3/5.75 + 1T | 2/6 | 3/2.5 + 2T |
| 23 | 0/0 | 1/1T | 3/3T | 4/10 | |
| 24 | 0/0 | 1/1T | absent | 4/13.5 | 6/9 + 3T |
| 25 | 0/0 | 0/0 | drop-out | | |
| 26 | 2/5 | 2/10.5 | 2/9.5 | 4/13.5 | |
| 27 | 0/0 | 2/2T | drop-out | | |
| 28 | 0/0 | 0/0 | drop-out | | |
| 29 | 0/0 | | 1/1T | 4/10.5 | 7/12.5 + 2T |

NOTE: Patient #8 was an HIV negative partner of participating patient. No skin tests were done on #8. Patient #22 did not complete initial 12 week phase of treatment. Patient #22 had only one skin test with 0/0 response.
Absent means that patient was not in attendance at clinic on the day scheduled for group skin tests.
Numbers to the left of the slash are the number of positive reactions. Numbers to the right of the slash are the total sizes of all positive reactions.
A "T" indicates that the size of the reaction is a trace.

There is clearly an increase in the number of positive skin reactions over the course of the study. Not surprisingly, since the overwhelming majority of patients had no reactions at intake, there was also an increase in the total size of all of the positive reactions ($p < 0.01$).

Summary

The following measurements were assessed on the twenty seven HIV-positive patients enrolled in the study:
1. The number of positive reactions to DTHS skin test antigens for cellular hypersensitivity at five points in time.
2. The total size of positive reactions to DTHS skin test antigens for cellular hypersensitivity at five points in time.

The results indicate significant improvement over the course of the study as indicated by increases in both the number of positive reactions to skin tests and the total size of those positive reactions.

II. Analysis of Karnofsky Performance Sales

Abstract

Twenty seven HIV-positive patients enrolled in the study were assessed on the Karnofsky Performance Scale at three points in time. Results indicate improvement over time with respect to percentage on this clinical classification system. A sample Karnofsky Performance scale is as follows:

| SAMPLE KARNOFSKY PERFORMANCE SCALE | | |
|---|---|---|
| Able to carry on normal activity; no special care is needed. | 100% | Normal, no complaints, no evidence of disease. |
| | 90% | Able to carry on normal activity; minor signs of disease. |

| SAMPLE KARNOFSKY PERFORMANCE SCALE -continued | | |
|---|---|---|
| | 80% | Normal activity with effort; some signs or symptoms of disease |
| Unable to work; able to live at home and care for most personal needs; a varying amount of assistance is needed. | 70% | Cares for self; unable to carry on normal activity or to do active work. |
| | 60% | Requires occasional assistance but is able to care for most of his needs. |
| | 50% | Requires considerable assistance and frequent medical care. |
| Unable to care for self; requires equivalent of institutional or hospital care; disease may be progressing rapidly. | 40% | Disabled; requires special care and assistance. |
| | 30% | Severely disabled; hospitalization is indicated although death not imminent. |
| | 20% | Very sick; hospitalization necessary; active supportive treatment is necessary. |
| | 10% | Moribund; fatal processes progressing rapidly. |
| | 0% | Dead. |

Results and Discussion

Significant improvement as measured by the Karnofsky score was noted between intake and March, 1991, for the eleven patients who had completed the Therapeutic phase of the treatment and were continuing on the Maintenance/Prophylaxis phases (p=0.0077). All eleven patients had Karnofsky scores of 100% in March, 1991, (see Tables 4–6). Further examination of the data indicated that these eleven patients exhibited significant improvement as early as February/March, 1990, when ten of the eleven had already achieved Karnofsky scores of 100%, and one patient had a score of 95%.

There was clear evidence of improvement in the eleven patients who continued in the study through March, 1991. All eleven patients achieved Karnofsky scores of 100% (ten reached this level as early as February/March, 1990, the one patient not at 100% at this time was at 95%). The four patients who completed the Therapeutic phase but did not continue with the full Maintenance/Prophylaxis phase had achieved scores of 100% by February/March, 1990. These four, as well as the twelve patients who withdrew between April and June, 1989, had comparable values at intake.

TABLE 4

KARNOFSKY SCORE DATA

| PATIENT # | INTAKE NOV/DEC 1988 OR AS NOTED | FEBRUARY/MARCH 1990 | MARCH 1991 |
|---|---|---|---|
| 1 | 90% | drop-out | |
| 2 | 90% | 100% | no maintenance |
| 3 | 90% | 50% drop-out returned for follow-up | |
| 4 | 100% (6/90) | 100% | 100% |
| 5 | 80% | drop-out | |
| 6 | 80% | 100% | 100% |
| 7 | 100% (2/89) | 100% | 100% |
| 9 | 80% (2/89) | 100% | some maintenance |
| 10 | 90% | drop-out | |
| 11 | 90% | drop-out | |
| 12 | 85% | 100% | 100% |
| 13 | 80% (6/89) | 100% | 100% |
| 14 | 90% (6/89) | 100% | 100% |
| 15 | 90% | 100% | 100% |
| 16 | 80% | drop-out | |
| 17 | 90% | drop-out | |
| 18 | 80% | died - (Ap-89) | |
| 19 | 80% | 100% drop-out returned for follow-up | |
| 20 | 90% | 100% | 100% |
| 21 | 80% | 100% | 100% |
| 23 | 90% | 100% | no maintenance |
| 24 | 90% | 100% | 100% |
| 25 | 80% | 60% drop-out returned for follow-up | |
| 26 | 80% | 100% | no maintenance |
| 27 | 80% | drop-out | |
| 28 | 90% | drop-out | |
| 29 | 70% | 90–100% | 100% |

NOTE: Patient #8 was an HIV negative partner of participating patient. Patient #22 did not complete initial 12 week phase of treatment.

TABLE 5
FREQUENCIES OF KARNOFSKY SCORES ALL AVAILABLE DATA

| KARNOFSKY SCORE | INTAKE | FEB/MARCH 1990 | MARCH 1991 |
|---|---|---|---|
| 50% | 0 | 1* (5.6%) | 0 |
| 60% | 0 | 1* (5.6%) | 0 |
| 70% | 1 (3.7%) | 0 | 0 |
| 80% | 11 (40.7%) | 0 | 0 |
| 85% | 1 (3.7%) | 0 | 0 |
| 90% | 12 (44.4%) | 0 | 0 |
| 95% | 0 | 1 (5.6%) | 0 |
| 100% | 2 (7.4%) | 15* (83.3%) | 11 (100%) |

*Three patients are included in Feb/March 1990 who had withdrawn from the study prior to this date. These are their scores (50%, 60%, 100%) when they returned for follow-up.

TABLE 6
FREQUENCIES OF KARNOFSKY SCORES FOR THE ELEVEN PATIENTS WHO COMPLETED THERAPEUTIC PLUS MAINTENANCE/PROPHYLAXIS TREATMENT

| KARNOFSKY SCORE | INTAKE | FEB/MARCH 1990 | MARCH 1991 |
|---|---|---|---|
| 70% | 1 (9%) | 0 | 0 |
| 80% | 3 (27%) | 0 | 0 |
| 85% | 1 (9%) | 0 | 0 |
| 90% | 4 (36%) | 0 | 0 |
| 95% | 0 | 1 (9%) | 0 |
| 100% | 2 (18%) | 10 (91%) | 11 (100%) |

Summary

Karnofsky Performance Scores were measured at three points in time. Patients who completed twelve months of the study reached the score of 100% by February, 1990. Those patients who continued with the Maintenance/Prophylaxis treatment maintained their score of 100% through February, 1991 (the last measurement point).

Those patients who completed the Therapeutic portion of the study scored between 95% and 100% on the Karnofsky Performance Scales. This is in contrast to the usual pattern that shows an unremitting decline with the passage of time.

III. Analysis of Body Weight and Oral Temperature Variability

These two basic Vital Signs were recorded weekly for all patients in the study. Although simple and easy to take, these criteria are strong indicators of patient stability or decline.

HIV positive patients are particularly vulnerable to various wasting diseases as they progress through the stages of AIDS. It was interesting to note that none of the patients exhibited wasting during any phase of this treatment.

In HIV patients, oral temperatures tend to be either excessively high or excessively low (as a result of active bacterial, viral fungal or other infection). Frequently, the active HIV patient exhibits a sub-normal temperature (approximately 97° F.) reflecting chronic, low grade viral infection. In almost all of the patients in this study, temperatures assumed normal profiles compared to intake values, and remained remarkably stable for the duration of each patient's treatment.

Abstract

Twenty seven HIV-positive patients enrolled in the study were monitored weekly for total body weight and oral temperature. Records indicate that no wasting syndrome was evident at any point in time for any patient. Temperatures were basically stable from week to week, with a greater proportion of temperature readings in the normal range as the study progressed.

Results and Discussion

The temperatures recorded for the patients as a whole are displayed in Table 7.

As shown in Table 7, the percentage of all readings which fell into the *normal* range increased steadily over the course of the study. At intake, 29.63% of the patients had normal temperatures. Between Weeks 1-12, the percentage rose to 50.18%. Weeks 13-24 show 61.40%, and Weeks 25-36 show 60.95%. After Week 37, the number of normal temperature readings shows another sizeable increase to 79.48%.

It should be pointed out that no wasting syndrome was experienced by any of the patients in the Study. In fact, records showed that 10 patients out of 27 (37.03%) actually gained weight during their participation in the Project.

TABLE 7

| | FREQUENCIES OF TEMPERATURE READINGS | | | | |
|---|---|---|---|---|---|
| TEMPERATURE | INTAKE | WEEKS 1-12 | WEEKS 13-24 | WEEKS 25-36 | WEEKS 37+ |
| >100 | 1 | 3 | 3 | 0 | 1 |
| (VERY HIGH) | (3.70%) | (1.10%) | (1.10%) | (0.00%) | (0.85%) |
| 99.1-100 | 1 | 13 | 13 | 4 | 2 |
| (HIGH) | (3.70%) | (4.76%) | (4.76%) | (3.81%) | (2.71%) |
| 98.2-99.0 | 8 | 137 | 167 | 64 | 93 |
| (NORMAL) | (29.63%) | (50.18%) | (61.40%) | (60.95%) | (79.48%) |
| 97.0-98.1 | 17 | 119 | 89 | 37 | 21 |
| (LOW) | (62.96%) | (43.59%) | (32.72%) | (35.24%) | (17.95%) |
| <97.0 | 0 | 1* | 0 | 0 | 0 |

TABLE 7-continued

| | FREQUENCIES OF TEMPERATURE READINGS | | | | |
|---|---|---|---|---|---|
| TEMPERATURE | INTAKE | WEEKS 1-12 | WEEKS 13-24 | WEEKS 25-36 | WEEKS 37+ |
| (VERY LOW) | (0.00%) | (0.37%) | (0.00%) | (0.00%) | (0.00%) |

*The one reading of "VERY LOW" represents a patient whose temperature was recorded as 94.8. It seems likely that this is a data entry error. However, it has been included in the table.

Summary

Both weights and temperatures were stable from week to week. The proportion of recorded temperatures in the normal range gradually became higher as the study progressed. Conversely, the proportion of chronically low temperatures decreased.

IV. Statistical Analysis Of Symptom Data Generated By Patients Who Completed Treatment And Maintenance Phases Of The Study

Abstract

Twenty-seven HIV-positive patients enrolled in the study were evaluated for the presence or absence of a series of forty symptoms presented from intake to two later points in time. Six scales were constructed as subsets of the original forty symptoms examined plus a TOTAL compilation. While borderline improvement was noted for one of the scales, significant improvement was evident for the other five scales. The TOTAL category (evaluation of overall number of symptoms present) also showed marked and progressive improvement.

The attached Tables 8 and 9 list the individual symptoms that have been grouped as follows:

Group 5 (symptoms most related to HIV disease progression)
Group 3 (symptoms moderately related to HIV disease progression)
Group 1 (symptoms mildly related to HIV disease progression)

The additional scales were:
FUNGAL (symptoms due to fungal infection)
QUALITY (daily quality of life)
WELL BEING (sense of well being)
TOTAL (all symptoms)

Results and Discussion

The results indicate that patients improved from intake to November, 1990. The mean number of symptoms per patient was reduced from 8.08 at intake to 1.73 in November (a decrease of 79%). This decrease was consistent across all of the scales. Group 5 symptoms decreased 87%, Group 3 symptoms decreased 67%, Group 1 symptoms decreased 87%, FUNGAL symptoms decreased 85%, WELL BEING symptoms decreased 85% and QUALITY symptoms decreased 76%. (See Table 10).

Summary

Data consisting of the presence or absence of a series of forty symptoms were collected on twelve patients infected with HIV at three points in time. The results indicate clear improvement from intake to November, 1990, as measured by the number of symptoms present. With the exception of one scale, "Sense of Well Being" in which improvement was only borderline, the other five scales all provide evidence indicative of significant improvement.

TABLE 8

TOTAL NUMBER OF SYMPTOMS AND MEAN NUMBER OF SYMPTOMS PER PATIENT*

| | INTAKE (NOV-DEC 1988) | MAY 1990 | NOVEMBER 1990 |
|---|---|---|---|
| TOTAL # OF SYMPTOMS | 97 (8.08) | 47 (3.92) | 19 (1.73) |
| GROUP 5 SYMPTOMS (SYMPTOMS MOST RELATED TO HIV PROGRESSION) | 34 (2.83) | 10 (0.83) | 4 (0.36) |
| BURNING MOUTH (THRUSH) | 1 | 1 | 0 |
| SHORTNESS OF BREATH | 3 | 0 | 0 |
| DIARRHEA | 2 | 0 | 0 |
| LACK OF APPETITE | 1 | 0 | 0 |
| BONE/MUSCLE ACHE | 5 | 2 | 1 |
| NIGHT SWEATS | 0 | 2 | 0 |
| ARTHRITIS-LIKE ACHES | 1 | 0 | 0 |
| TROUBLE BREATHING | 1 | 0 | 0 |
| FATIGUE | 7 | 2 | 1 |
| ATHLETE'S FOOT | 4 | 1 | 1 |
| JOCK ITCH | 2 | 0 | 0 |
| FINGER/TOE NAIL FUNGUS | 3 | 2 | 1 |
| LACK OF SEXUAL DESIRE | 2 | 0 | 0 |
| BURN/ITCH/GROIN/SCROTUM | 1 | 0 | 0 |
| VAGINAL ITCH | 1 | 0 | 0 |
| VAGINAL BURNING | 0 | 0 | 0 |
| VAGINAL SORENESS | 0 | 0 | 0 |
| GROUP 3 SYMPTOMS (SYMPTOMS MODERATELY RELATED TO HIV PROGRESSION) | 39 (3.25) | 24 (2.00) | 12 (1.08) |
| HEADACHE | 4 | 2 | 1 |
| COUGH | 3 | 0 | 0 |
| CLOUDY EYESIGHT | 3 | 2 | 1 |
| SORE THROAT | 1 | 0 | 0 |
| BLEEDING GUMS | 3 | 2 | 1 |

TABLE 8-continued

TOTAL NUMBER OF SYMPTOMS AND MEAN NUMBER OF SYMPTOMS PER PATIENT*

| | INTAKE (NOV-DEC 1988) | MAY 1990 | NOVEMBER 1990 |
|---|---|---|---|
| HAIR LOSS | 1 | 0 | 0 |
| EYE FOCUS PROBLEMS | 5 | 1 | 0 |
| TROUBLE SLEEPING | 3 | 2 | 1 |
| BUMPS THAT ITCH | 3 | 2 | 0 |
| SWOLLEN GLANDS | 5 | 5 | 5 |
| UNFRESHED SLEEP | 5 | 5 | 3 |
| DEPRESSION | 3 | 3 | 0 |

*Means appear in parentheses

TABLE 9

TOTAL NUMBER OF SYMPTOMS AND MEAN NUMBER OF SYMPTOMS PER PATIENT*

| | INTAKE (NOV-DEC 1988) | MAY 1990 | NOVEMBER 1990 |
|---|---|---|---|
| GROUP 1 SYMPTOMS SYMPTOMS MILDLY RELATED TO HIV PROGRESSION) | 24 (2.00) | 13 (1.08) | 3 (0.27) |
| SINUS TROUBLE | 1 | 2 | 1 |
| COLDS | 2 | 0 | 0 |
| SORE GUMS | 1 | 2 | 0 |
| COLD HANDS/FEET | 3 | 1 | 0 |
| TINGLING SKIN | 1 | 0 | 0 |
| LOSS OF CONCENTRATION | 3 | 2 | 0 |
| MOOD CHANGES | 5 | 2 | 1 |
| ANXIOUSNESS | 4 | 4 | 1 |
| VAGINAL INFECTION | 1 | 0 | 0 |
| VAGINAL DISCHARGE | 2 | 0 | 0 |
| IRREGULAR PERIODS | 1 | 0 | 0 |
| FUNGAL SYMPTOMS | 14 (1.17) | 4 (0.33) | 2 (0.18) |
| BURNING MOUTH (THRUSH) | | | |
| ATHLETE'S FOOT | | | |
| JOCK ITCH | | | |
| FINGER/TOE NAIL FUNGUS | | | |
| BURN/ITCH/GROIN/SCROTUM | | | |
| VAGINAL ITCH | | | |
| VAGINAL BURNING | | | |
| VAGINAL SORENESS | | | |
| VAGINAL DISCHARGE | | | |
| SENSE OF WELL BEING SYMPTOMS | 14 (1.17) | 8 (0.67) | 2 (0.18) |
| LACK OF SEXUAL DESIRE | | | |
| LOSS OF CONCENTRATION | | | |
| MOOD CHANGES | | | |
| ANXIOUSNESS | | | |
| QUALITY OF LIFE SYMPTOMS | 27 (2.25) | 16 (1.33) | 6 (0.55) |
| HEADACHE | | | |
| SHORTNESS OF BREATH | | | |
| DIARRHEA | | | |
| TROUBLE SLEEPING | | | |
| NIGHT SWEATS | | | |
| FATIGUE | | | |
| UNFRESHED SLEEP | | | |
| DEPRESSION | | | |

*Means appear in parenthesis

TABLE 10

PERCENTAGE DECREASE IN THE NUMBER OF SYMPTOMS PRESENT

| | INTAKE TO MAY 1990 (18 MONTHS) | MAY 1990 TO NOVEMBER 1990 (6 MONTHS) | INTAKE TO NOVEMBER 1990 (24 MONTHS) |
|---|---|---|---|
| TOTAL # OF SYMPTOMS | 50% decrease | 56% decrease | 79% decrease |
| GROUP 5 (SYMPTOMS MOST RELATED TO HIV PROGRESSION) | 71% decrease | 57% decrease | 87% decrease |
| GROUP 3 (SYMPTOMS MODERATELY RELATED TO HIV PROGRESSION) | 38% decrease | 46% decrease | 67% decrease |
| GROUP 1 | 46% decrease | 75% decrease | 87% decrease |

TABLE 10-continued

PERCENTAGE DECREASE IN THE NUMBER OF SYMPTOMS PRESENT

| | INTAKE TO MAY 1990 (18 MONTHS) | MAY 1990 TO NOVEMBER 1990 (6 MONTHS) | INTAKE TO NOVEMBER 1990 (24 MONTHS) |
|---|---|---|---|
| (SYMPTOMS MILDLY RELATED TO HIV PROGRESSION) | | | |
| FUNGAL SYMPTOMS | 71% decrease | 45% decrease | 85% decrease |
| SENSE OF WELL BEING SYMPTOMS | 43% decrease | 73% decrease | 85% decrease |
| QUALITY OF LIFE SYMPTOMS | 41% decrease | 62% decrease | 76% decrease |

*Intake was from November to December 1988

V. Statistical Analysis of Drug Related Toxicity As Indicated by SGOT and SGPT These two basic laboratory markers (SGOT and SGPT) function as widely accepted indicators of liver function in relation to drug toxicity. However, several factors should be noted in conjunction with these measurements.

As expressed in Clinical Interpretation of Laboratory Tests (Ninth Edition) Frances K. Widmann, M.D., a medical textbook on the diagnostic use of laboratory procedures noted:

"The two enzymes most often associated with hepatocellular damage are aminotransferases that catalyze the reversible transfer to an amino group between an amino acid and an alpha-keto acid. The enzymes are called glutamic-oxaloacetic transaminase (GOT) and glutamic-pyruvic transaminase (GPT)."

"Because the liver has such substantial reserve capacity, hepatocellular loss must be far advanced before it becomes clinically apparent. It is possible to detect ongoing hepatocellular damage by measuring functional indices and by observing in the circulation the products of damaged or necrotic hepatocytes. Enzyme tests are often the only indications of early or localized liver disease."

When measured with the serum, these tests are often called SGOT and SGPT.

In the HIV-positive patient population, these two values may be elevated when baseline bloodwork is performed. This elevation can be caused by hepatitis (either chronic or acute), acute viral infections (such as Hepatitis B or EBV), cirrhosis of the liver or previous use of recreational drugs (such as heroin). In spite of these potential complications, SGOT and SGPT can be used to evaluate toxicity of any drug being administered.

When a patient's baseline values are within a normal range, a dangerous toxic reaction would be indicated by readings of four-times the maximum normal range. If a patient presents with elevated liver enzymes, judgment concerning toxicity must be based on evaluation of two factors: how high the actual elevation is and also how quickly it becomes evident.

Only one patient showed a pattern unlike the others. He experienced a sudden, acute elevation of these blood markers during the last three recorded weeks of treatment. It is reported that, when questioned by the Head Nurse, he admitted that he had begun an additional treatment modality. By mutual agreement, he terminated his participation in this study.

All other patients in this study showed no evidence of toxicity induced by the medicaments used for treatment. In fact, blood tests showed that many patients who entered the study with considerable elevation in both SGOT and SGPT demonstrated significant decrease from the original high levels. Those who entered with relatively normal values either further decreased or remained at the same level. It is notable that no treatment related toxicity developed in any patient during the entire period of the study.

Abstract

Levels of two liver enzymes, SGOT and SGPT, were measured weekly for up to sixty weeks on the patients enrolled in the study to assess drug related toxicity. These tests indicated that levels of both SGOT and SGPT remained stable over the course of treatment. The percentage of observations that fell within normal ranges for both SGOT and SGPT also remained stable over time.

Results and Discussion

Table 11 lists the median levels of SGOT and SGPT of all measurements on each patient at intake and then at four more time intervals:
A. Week 1 to Week 12
B. Week 13 to Week 24
C. Week 25 to Week 36
D. Week 37 to the final measurement The number and percentage of times these measures were in the normal range and above the normal range are listed in Table 12.

The percentage of normal measures is seen to be quite stable over time. As with the medians, the percentage of times that measures were in the normal range appears to improve substantially after 36 weeks. For median SGPT levels, the largest improvement occurred after 24 weeks. However, the later time intervals include proportionately more of the patients who had remained in treatment then do the earlier intervals.

Summary

The available data on these patients indicates that drug related toxicity did not increase over time. Further, medians of all observations and the percentage of observations in normal ranges remained stable over the course of the study. It can be stated that the medicaments administered to the patients did not cause any drug related toxicity.

TABLE 11

| MEDIANS OF SGOT AND SGPT USING ALL AVAILABLE DATA | | | | | |
|---|---|---|---|---|---|
| | INTAKE | TREATMENT WEEKS 1-12 | TREATMENT WEEKS 13-24 | TREATMENT WEEKS 25-36 | TREATMENT WEEKS 37+ |
| SGOT | | | | | |
| MEDIAN | 36.00 | 37.50 | 37.50 | 37.00 | 34.00 |
| SGPT | | | | | |
| MEDIAN | 33.00 | 38.50 | 34.00 | 28.00 | 27.50 |
| NUMBER OF TESTS | 27 | 274 | 264 | 117 | 104 |

TABLE 12

| COMPARISON OF NUMBER AND PERCENT OF SGOT AND SGPT TEST RESULTS WITHIN NORMAL RANGE AND ABOVE NORMAL RANGE | | | | | |
|---|---|---|---|---|---|
| | INTAKE | TREATMENT WEEKS 1-12 | TREATMENT WEEKS 13-24 | TREATMENT WEEKS 25-36 | TREATMENT WEEKS 37+ |
| SGOT | | | | | |
| NORMAL RANGE | | | | | |
| NUMBER | 19 | 162 | 157 | 80 | 69 |
| PERCENT | 70.4% | 59.1% | 57.3% | 59.8% | 66.3% |
| ABOVE NORMAL RANGE | | | | | |
| NUMBER | 8 | 112 | 107 | 47 | 35 |
| PERCENT | 29.6% | 40.9% | 42.7% | 40.2% | 33.7% |
| SGPT | | | | | |
| NORMAL RANGE | | | | | |
| NUMBER | 20 | 217 | 208 | 95 | 93 |
| PERCENT | 74.1% | 79.2% | 78.8% | 81.2% | 89.4% |
| ABOVE NORMAL RANGE | | | | | |
| NUMBER | 7 | 57 | 56 | 22 | 11 |
| PERCENT | 25.9% | 20.8% | 21.2% | 18.8% | 10.6% |

VI. Additional Clinical Findings at the Conclusion of Therapeutic Phase of the Study The Patient Population was divided into two segments.

A. ACTIVE—Those who completed the full study and have remained on the maintenance portion of the program. (12 patients)
B. DROP-OUTS—Those who left before the end of the study and never completed treatment.

Group A: (Active)

Upon final examination, all the patients in Group A had fairly normal physical examinations and a healthy robust appearance. Two of the patients stated that they had problems with psoriasis which were much improved over the course of therapy.

One patient in Group A developed Hairy Leukoplakia after UV therapy for folliculitis, but this was resolved after cessation of the UV therapy.

Mood Changes: Many instances of depression and other emotional problems were reported in the intake histories. With the Exception of a single patient who opted to return to the mood elevating drugs he had formerly been taking, all of the patients exhibited generally cheerful, optimistic outlooks.

Fatigue: Initially, there were subjective complaints of fatigue by most of the patients. At the conclusion of the study, all 12 patients are leading normal lives and are working. All generally stated that they had increased levels of energy.

Pulse: Initially many pulse rates were rapid and approximately 90. At the conclusion of the treatment, all patients exhibited strong, regular pulse of 60-75.

Night sweats: Many patients complained of recurrent episodes of this malady upon entering the study. None reported any incidents of the problem when questioned at the conclusion of treatment.

General physical stamina: According to preliminary reports, several patients complained of limited physical strength and, in one instance, one patient presented with arthritis sufficiently severe that he could only walk with the aid of two canes. At the final examination, all reported that they were leading normal and demanding, fully strenuous physical lives. Many of them resumed regular workout sessions at the gym and one worked weekends unloading trucks.

Non-Development of AIDS Defining Disease Conditions: Almost none of the ancillary diseases that may be expected to become evident in the patient population during the course of a study occurred. The following disease entities did NOT become evident in the patients during at least the 18 month time span after the start of the study.

1. Pneumocystis Carinii Pneumonia
2. Candidiasis of the esophagus, trachea, bronchi or lungs.
3. Extrapulmonary Cryptococcosis
4. Cryptosporidiosis with diarrhea
5. Cytomegalovirus disease of an organ
6. Herpes Simplex virus infection with persisting mucocutaneous ulcer
7. Karposi's sarcoma
8. Primary lymphoma of the brain
9. *Mycobacterium avium*
10. Progressive multi-focal leukoencephalopathy
11. Toxoplasmosis of the brain
12. Coccidioidomycosis
13. Histoplasmosis
14. Isospororsis
15. Non-Hodgkins lymphoma of any type 16. Pulmonary tuberculosis
17. *Salmonella septicemia*

Alleviation of AIDS Related Conditions: The following medical problems, when originally present, were either resolved or significantly improved during the study so that at the end of the study the patients were essentially symptom free:
1. Oral Hairy Leukoplakia
2. Persistent fungal infections including thrush, athletes foot, jock itch, onychomycosis, etc.
3. Lymphadenopathy
4. Reiters Syndrome
5. Guillain-Barre Syndrome
6. Gastrointestinal complaints
7. Various viral conditions such as:
   Herpes Simplex
   Herpes Zoster (shingles)
8. Psoriasis
9. Syphilis

Group B (Drop-Outs)

Three of the patients in Group B had, for the most part, fairly normal physical examinations. Two of them had developed Hairy Leukoplakia. One case, according to the patient, had resolved with a course of Zovirax. Two of these patients went on AZT, although one was intolerant to the therapy and had to discontinue it. One is taking Zovirax. However, the subjective impression of these three patients was that they appeared healthier than would be the normal pattern at this phase of the disease. In general they seemed to be in good shape.

Two patients were significantly worse physically with a frank diagnosis of AIDS. Both had developed *Pneumocystis pneumonia* (PCP); one had developed cryptococcal meningitis and had progressive Karposi's Sarcoma; the other had thrush, wasting and fatigue at the time of examination.

No clinical examination was possible on the remaining patients.

VII. Final Impressions

If one compares the natural history of HIV, with average T-4 cells in the low 300's, a progressive decline in the health status of these patients could be expected over the 18 months duration of this treatment. Additionally, more and more frequent occurrence of illnesses, general fatigue and ongoing weight loss could be expected. However, none of this occurred in the study.

In general, two years after intake, the Study patient population could be expected to present with an extensive range of opportunistic diseases. Instead, with the minor clinical exceptions noted above, the patients were in good health.

As already discussed, it is important to note that, although many of the test procedures described above deal with AIDS, the same procedures also relate to the medical problems that affect the non-AIDS patient population.

AIDS is not a single disease. Although much of the media coverage has given this impression, AIDS is not merely the HIV virus.

Just as the name indicates, AIDS is a syndrome or collection of medical conditions. The element that binds AIDS patients together is that they all have a compromised immune system. Beyond this, a wide range of other disease entities can be present or absent. The list of possibilities includes intestinal parasites, systemic fungus (*Candida albicans* and others), viral diseases (EBV, CMV, herpes, hepatitis, etc.), bacterial problems (Staph, Strep, etc.), tuberculosis, syphilis, etc.

None of these disease entities are unique to AIDS. They also afflict the general public either in the form of individual diseases or else in such groupings as Chronic Fatigue Syndrome (CFS). For this reason, the method, procedures and individual medicaments that treat AIDS have applications that extend far beyond that.

The terms and expressions which have been employed are used as terms of description and not of limitation, and there is no intention in the use of such terms or expressions of excluding any equivalents of the features shown and described or portions thereof, it being recognized that various modifications are possible within the scope of the invention.

What is claimed is:

1. A method for treating pathogenic conditions of the human body comprising the steps of:
   preparing a mixture of at least one herb, herbal extract or other compound having therapeutic properties to which a particular condition being treated is responsive;
   adding a magnetically permeable substance to the mixture if necessary;
   magnetizing the resulting mixture in a magnetic field during delivery to impart a substantially unipolar magnetic charge on said mixture; and
   administering the magnetized mixture through one or more specific acupuncture points of the body which are associated with producing a desired response to the particular condition being treated.

2. The method of claim 1 wherein the mixture is magnetized in a magnetic field of less than ten gauss.

3. The method of claim 1 wherein the magnetized mixture is topically administered to the body.

4. The method of claim 3 wherein a therapeutic amount of the magnetized mixture is placed over at least one pair of bilateral acupuncture points on the surface of the body.

5. The method of claim 4 wherein the mixture is magnetized by placing a source of magnetic flux in proximity to the mixture while it is placed over the bilateral acupuncture points on the surface of the body.

6. The method of claim 1 wherein the magnetized mixture is injectably administered to the body.

7. The method of claim 6 wherein a therapeutic amount of the magnetized mixture is injected into at least one pair of bilateral acupuncture points of the body.

8. The method of claim 1 wherein the magnetized mixture is auricularly administered to the body.

9. The method of claim 8 wherein a therapeutic amount of the magnetized mixture is impregnated into metal rods inserted into a device fitted to be placed over the ear, the metal rods being located in said device such that the magnetized mixture is in contact with at least one auricular acupuncture point when the device is placed over the ear.

10. The method of claim 1 wherein the magnetized mixture is orally administered to the body.

11. The method of claim 10 wherein a therapeutic amount of the magnetized mixture is administered to acupuncture points in the mouth by means of an oral delivery device which is magnetically transparent and permeable comprising a rod portion connected to a porous ball portion, said rod portion being capable of accepting and holding a magnetic charge, and said ball portion being impregnated with an effective amount of said mixture, wherein said rod portion of the device is magnetized so that the desired charge is at the ball portion, and wherein the patient places the ball portion of the device under the tongue to influence the acupuncture points.

12. A method for the treatment of conditions of the human body including injuries, illnesses, pathogenic diseases, allergies and chemical and hormonal imbalances, the method comprising the administration of a combination of oral, injectable and topical forms of a therapeutic amount of a magnetized solution containing a solute of one or more therapeutic herbs or herbal extracts or other compounds having properties to which the particular condition being treated is responsive, the solute being dissolved in a vehicle, where the vehicle for the oral and topical form is a mixture of 99+% alcohol, and the vehicle for the injectable form is a mixture of 99+% alcohol diluted with sterile isotonic saline, together with a magnetically permeable, non-toxic substance if necessary; and wherein the oral form is impregnated into a solid placed in the mouth to release the magnetized mixture contained therein, thereby stimulating acupuncture points in the mouth; wherein the topical form is also impregnated into a solid and affixed as a transdermal patch to at least one suitable acupuncture point; and wherein the injectable form is injected into at least one specific acupuncture point of the body related to the part of the body or the condition being treated; the oral, topical and injectable treatments being administered in appropriate dosages for a sufficient period of time depending on the severity of the condition and the response of the patient being treated, with provision for a further period of maintenance treatments of different dosage and frequency of administration where symptoms of the condition persist.

13. The method of claim 12 wherein the condition being treated is traumatic injury to one or more joints, muscles, tendons and ligaments and the solute of the magnetized solution comprises an effective amount of one or more herbs or extracts selected from the group consisting of *Arnica Montana, Symphytum officianalis, Moschus moschiferous,* Cow bezoar, *Pupalia geniculata,* Snake's gall, *Rhus Toxicum,* Germanuim dioxide, *Plantago asiatica,* Causticum, *Helianthemum canadense, Ornithogalum umbellatum, Clematis crispa, Impatiens pallida, Prunus Cerasus* and pineal gland.

14. The method of claim 12 wherein the oral dosage is a metal rod and sphere impregnated with a solution having a homeopathic potency of 30X, administered initially as one rod and sphere per day, reduced to one every other day and finally to once per week over the course of treatment; wherein the topical dosage is a transdermal patch, impregnated with a solution having a homeopathic potency of 30X, placed over at least one acupuncture point two times per week for a first phase of treatment and once per week on successive weeks over a maintenance phase of treatment; wherein the injectable dosage is an injection of 0.2 cc per acupuncture point of the injectable solution having a homeopathic potency of 30X, administered to the acupuncture points and related local acupuncture points for the specific injured member being treated, the injections being given initially 2 times per week for a first phase of treatment and once per week on successive weeks over the balance of a therapeutic phase as well as a maintenance phase of treatment; and wherein the duration of the oral, topical and injectable modes of treatment is from about 12 weeks, followed by a period of maintenance for as long as symptoms of the condition persist.

15. The method of claim 12 wherein the condition being treated is hypothyroidism and the solute of the magnetized solution comprises an extract of thyroid gland.

16. The method of claim 15 wherein the injectable and topical dosages are administered bilaterally to each of the two LI-11 acupuncture points 2 times per week for the first week of treatment and once per week on successive weeks over the course of treatment; and wherein the duration of the oral, topical and injectable modes of treatment is six weeks, followed by a period of maintenance of several weeks for as long as the symptoms of the condition persist.

17. The method of claim 12 wherein the condition being treated is one or more of pre-menstrual syndrome, menopause and reproductive hormonal imbalance in female human beings and the solute of the magnetized solution comprises the herb *Angelica sinensis* or an extract thereof and an extract of pineal gland.

18. The method of claim 15 wherein the injectable and topical dosages are administered bilaterally to each of the two LI-11 acupuncture points from 1 to 2 times per week for the first week of treatment and once per week on successive weeks over the course of treatment; and wherein the duration of the oral, topical and injectable modes of treatment is from 4 to 8 weeks, followed by a period of maintenance of several weeks for as long as the symptoms of the condition persist.

19. The method of claim 12 wherein the condition being treated is emotional depression and tension, and the solute of the magnetized solution comprises one or more herbs or herbal extracts selected from the group consisting of *Helianthemum canadense, Ornithogalum umbellatum, Clematis crispa, Impatiens pallida, Prunus cerasus, Valeriana officinalis* and pineal gland.

20. The method of claim 17 wherein the injectable and topical dosages are administered bilaterally to the SP-6 acupuncture points a total of four to six times, followed by a period of maintenance of several weeks for as long as symptoms of the condition persist.

21. The method of claim 12 wherein the condition being treated is a reduction in the body's natural immune system and the solute of the magnetized solution comprises one or more herbs or extracts selected from the group consisting of *Panex ginseng, Astragalus membranaceous,* Snake venom, thymus gland, *Rubia cordifolia* and pineal gland.

22. The method of claim 20 wherein the injectable and topical dosages are administered bilaterally to one of the following pairs of acupuncture points: HE-5, HE-6 and HE-7, given 2 times per week for the first week of treatment and once per week on successive weeks over the course of treatment; and wherein the duration of the oral, topical and injectable modes of treatment is 6 weeks, followed by a period of maintenance of several weeks for as long as symptoms of the condition persist.

23. The method of claim 22 wherein the injectable and topical dosages are administered bilaterally to each of the two LI-4 acupuncture points 2 times per week for the first week of treatment and once per week on successive weeks over the course of treatment; and wherein the duration of the oral, topical and injectable modes of treatment is 6 to 8 weeks, followed by a period of maintenance of several weeks for as long as the symptoms of the condition persist.

24. The method of claim 12 wherein the condition being treated is hypoglycemia and the solute of the magnetized solution comprises a mixture of sulfur and glycerin.

25. The method of claim 24 wherein the injectable and topical dosages are administered bilaterally to each of the two ST-36 acupuncture points, given 2 times per week for the first week of treatment and one per week on successive weeks over the course of treatment; and wherein the duration of the oral, topical and injectable modes of treatment is from 6 to 8 weeks, followed by a period of maintenance of several weeks for as long as symptoms of the condition persist.

26. The method of claim 12 wherein the condition being treated is a general or localized bacterial infection of the body, and the solute of the magnetized solution comprises one or more herbs or extracts selected from the group consisting of *Seniccio scandens, Scutellaria baicalensis, Magnolia officinalis, Lonicera japonica, Andrographis paniculata, Centella asiatica minor, Leptotaenia multifida, Moschus moschiferous,* Cow bezoar, *Pupalia geniculata,* Snake's gall and pineal gland.

27. The method of claim 26 wherein the injectable and topical dosages have a homeopathic potency of 30×, and are administered bilaterally to each of the two IL-11 acupuncture points, given 2 times per weeks for the first week of treatment and one per week on successive weeks over the course of treatment; and wherein the duration of the oral, topical and injectable modes of treatment is 6 to 12 weeks depending on the pathogen being treated, followed by a period of maintenance of several weeks for as long as the symptoms of the condition persist.

28. The method of claim 12 wherein the condition being treated is a general virus infection of the body and the solute of the magnetized solution comprises one or more herbs or extracts selected from the group consisting of *Centella asiatica minor, Pyrrosia lingua, Hypericum perfoliatum, Trichosanthes Kirilowii, Artemasia apiacea* and pineal gland.

29. The method of claim 28 wherein the injectable and topical dosages have a homeopathic potency of 30×, and are administered bilaterally to each of the two TW-5 acupuncture points, given 1 or 2 times per week for the first week of treatment and once per week on successive weeks over the course of treatment; and wherein the duration of the oral, topical and injectable modes of treatment is from 8 to 12 weeks, followed by a period of maintenance of several weeks for as long as symptoms of the condition persist.

30. The method of claim 12 wherein the condition being treated is a cold caused by the rhino-virus or influenza and the solute of the magnetized solution comprises one or more herbs or extracts selected from the group consisting of *Lonicera confusa, Chrysanthemum indicum, Vitex negundo, Evodia lepta, Ilex asprella, Menthol crystal, Baphicacanthus cusia, Centella asiatica minor* and pineal gland.

31. The method of claim 30 wherein the injectable and topical dosages are administered bilaterally to each of the two TW-5 acupuncture points, given 2 times per week for the first week of treatment and once per week on successive weeks over the course of treatment; and wherein the duration of the oral, topical and injectable modes of treatment is three weeks, followed by a period of maintenance of several weeks for as long as symptoms of the condition persist.

32. The method of claim 12 wherein the condition being treated is one or more of hay fever and airborne allergies, and the solute of the magnetized solution comprises one or more herbs or extracts selected from the group consisting of *Gentiana luta, Citrus aurantium, Tanacetum vulgare, Cnicus benedictus, Menyanthes trifoliata, Grindelia robusta, Ephedra sinica, Centipeda minima,* pineal gland and *Centella asiatica minor.*

33. The method of claim 32 wherein the injectable and topical dosages are administered bilaterally to each of the two PE-6 acupuncture points or the auricular lung point, given 2 times per week for the first week of treatment and once per week on successive weeks over the course of treatment; and wherein the duration of both the oral and injectable modes of treatment is from 2 to 4 weeks, followed by a period of maintenance of several weeks for as long as the symptoms of the condition persist.

34. The method of claim 12 wherein the condition being treated is one or more of local and systemic fungus and yeast infections, and the solute of the magnetized solution comprises one or more herbs or extracts selected from the group consisting of *Malaleuca alternifolio, Centella asiatica minor,* citrus seed, *Tacoma conspicus* and pineal gland.

35. The method of claim 34 wherein the injectable and topical dosages are administered bilaterally to the SP-6 acupuncture point, given 2 times per week for the first week of treatment and once per week on successive weeks over the course of treatment; and wherein the duration of the oral, topical and injectable modes of treatment is from 6 to 12 weeks, followed by a period of maintenance of several weeks for as long as symptoms of the condition persist.

36. The method of claim 12 wherein the condition being treated is infestation with intestinal parasites and the solute of the magnetized solution comprises one or more herbs or extracts selected from the group consisting of *Osbeckia chinensis, Pulsattila chinensis, Punica granatum, Acalpha australis, Cephaelis ipecacuanha, Picrasma ailanthoides, Asarum sieboldi, Brucea javanica, Magnolia officinalis, Artemisia apiacea, Dichroa febrifuga, Centella asiatica minor,* citrus seed and pineal gland.

37. The method of claim 36 wherein the injectable and topical dosages are administered bilaterally to the ST-36 and ST-37 acupuncture points which are used alternately and treatments are given 2 times per week for the first week and once per week on successive weeks over the course of treatment; and wherein the duration of both the oral and injectable modes of treatment is from six to eight weeks, followed by a period of maintenance of several weeks if required.

38. The method of claim 12 wherein the condition being treated is acute or chronic muscular and joint pain and the solute of the magnetized solution comprises one or more herbs or extracts selected from the group consisting of *Arnica Montana, Symphytum officianalis, Moschus moschiferous,* Cow bezoar, *Pupalia geniculata,* Snake's gall, *Rhus Toxicum, Germanuim dioxide, Plantago asiatica,* Causticum, *Helianthemum canadense, Ornithogalum umbellatum, Clematis crispa, Impatiens pallida, Prunus Cerasus* and pineal gland.

* * * * *